(12) United States Patent
Fujita et al.

(10) Patent No.: US 7,470,231 B2
(45) Date of Patent: Dec. 30, 2008

(54) FATIGUE DEGREE MEASUREMENT DEVICE, FATIGUE DETECTION DEVICE AND COMPUTER PROGRAM TO BE USED THEREIN

(75) Inventors: Etsunori Fujita, Hiroshima (JP); Shigehiko Kaneko, Kawaguchi (JP)

(73) Assignee: Delta Tooling Co., Ltd., Hiroshima (JP)

( * ) Notice: Subject to any disclaimer, the term of this patent is extended or adjusted under 35 U.S.C. 154(b) by 2 days.

(21) Appl. No.: 10/576,173

(22) PCT Filed: Oct. 22, 2004

(86) PCT No.: PCT/JP2004/016058

§ 371 (c)(1),
(2), (4) Date: Oct. 27, 2006

(87) PCT Pub. No.: WO2005/039415

PCT Pub. Date: May 6, 2005

(65) Prior Publication Data

US 2007/0078351 A1     Apr. 5, 2007

(30) Foreign Application Priority Data

Oct. 23, 2003     (JP) ............................. 2003-363902

(51) Int. Cl.
*A61B 5/00* (2006.01)
(52) U.S. Cl. .................................. 600/300
(58) Field of Classification Search ................. 600/481, 600/300
See application file for complete search history.

(56) References Cited

U.S. PATENT DOCUMENTS

| | | | |
|---|---|---|---|
| 6,261,235 B1 | 7/2001 | Amano et al. | |
| 6,364,842 B1 | 4/2002 | Amano et al. | |
| 6,767,329 B2 | 7/2004 | Amano et al. | |
| 2002/0065471 A1 | 5/2002 | Amano et al. | |
| 2002/0156392 A1* | 10/2002 | Arai et al. ............ | 600/546 |
| 2004/0137639 A1 | 7/2004 | Miyazaki et al. | |
| 2004/0236235 A1* | 11/2004 | Fujita et al. .............. | 600/500 |
| 2006/0247542 A1* | 11/2006 | Watanabe et al. ......... | 600/500 |

FOREIGN PATENT DOCUMENTS

| | | |
|---|---|---|
| CN | 1102036 | 11/2003 |
| DE | 694 31 575 T2 | 3/2003 |
| EP | 0 630 608 A1 | 12/1994 |

(Continued)

*Primary Examiner*—Charles A. Marmor, II
*Assistant Examiner*—Christian Y Jang
(74) *Attorney, Agent, or Firm*—WolfBlock LLP

(57) ABSTRACT

A fatigue degree measurement device includes a living body signal peak value detecting step to detect the peak values of respective cycles of the original waveform of the living body signal data; a power value calculating step to calculate the difference between a peak value on the upper limit side and a peak value on the lower limit side for every prescribed time period from respective peak values obtained by the living body signal peak value detecting step to set the difference as a power value; and a power value inclination calculating step to determine the inclination of the power value, to calculate an integral value by absolute value treatment of the time series signals of the inclination of the power values to determine the integral value as the degree of fatigue.

12 Claims, 17 Drawing Sheets

FOREIGN PATENT DOCUMENTS

| | | |
|---|---|---|
| EP | 0 630 608 B1 | 12/1994 |
| JP | 3039236 | 2/1991 |
| JP | 3047712 | 2/1991 |
| JP | 3049987 | 3/1991 |
| JP | 3070327 | 3/1991 |
| JP | 3070346 | 3/1991 |
| JP | 3092369 | 4/1991 |
| JP | 6-009546 | 2/1994 |
| JP | 6-205747 | 7/1994 |
| JP | 6-254060 | 9/1994 |
| JP | 6-261870 | 9/1994 |
| JP | 7-136139 | 5/1995 |
| JP | 7-148126 | 6/1995 |
| WO | WO 94/15526 | 7/1994 |
| WO | WO 02/087434 A1 | 11/2002 |

\* cited by examiner

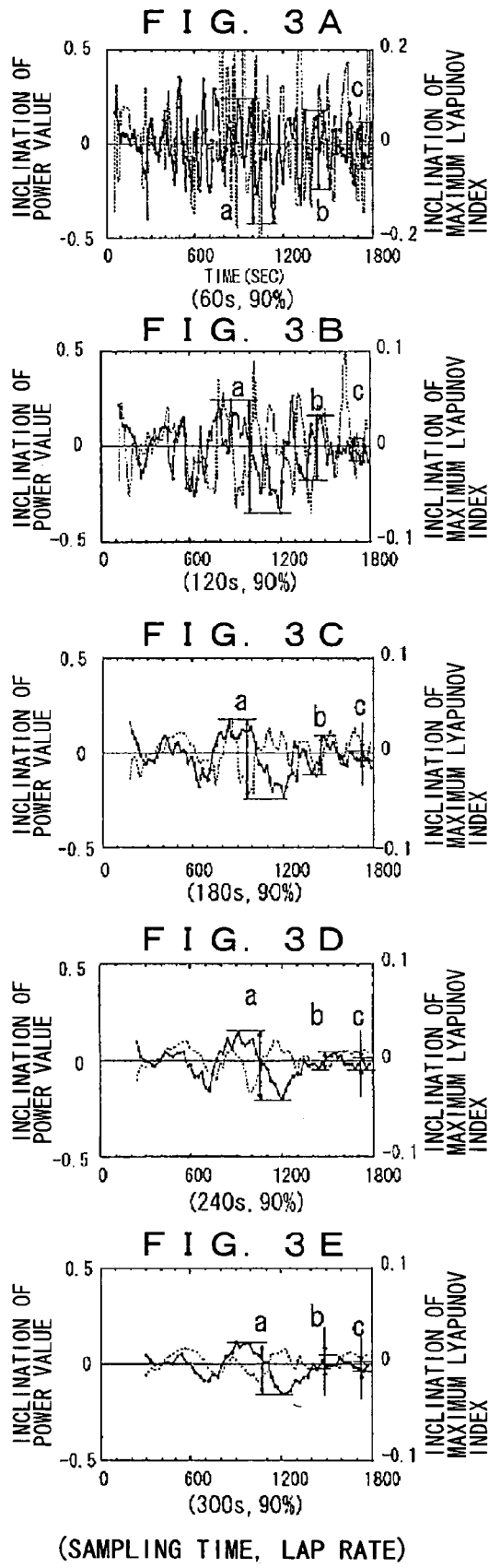
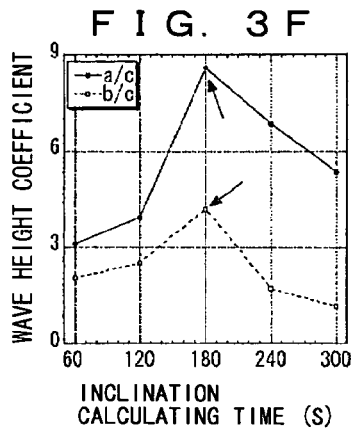
SLIDE CALCULATION LAP RATE = 90%
COMPARISON OF WAVE HEIGHT COEFFICIENT BASED ON SAMPLING TIME
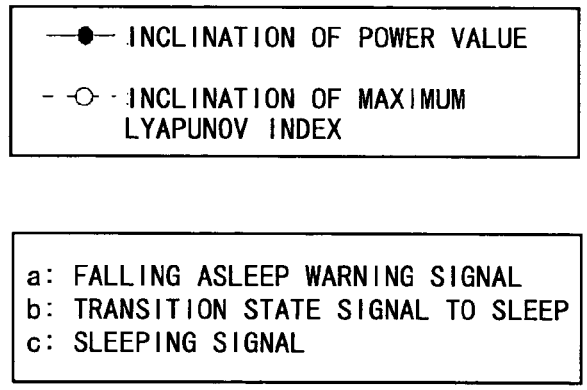
a: FALLING ASLEEP WARNING SIGNAL
b: TRANSITION STATE SIGNAL TO SLEEP
c: SLEEPING SIGNAL
(SAMPLING TIME, LAP RATE)

INCLINATION CALCULATING TIME = 180s

COMPARISON OF WAVE HEIGHT COEFFICIENT BASED ON LAP RATE

- — ● — INCLINATION OF POWER VALUE
- - ○ - INCLINATION OF MAXIMUM LYAPUNOV INDEX a: FALLING ASLEEP WARNING SIGNAL
b: TRANSITION STATE SIGNAL TO SLEEP
c: SLEEPING SIGNAL

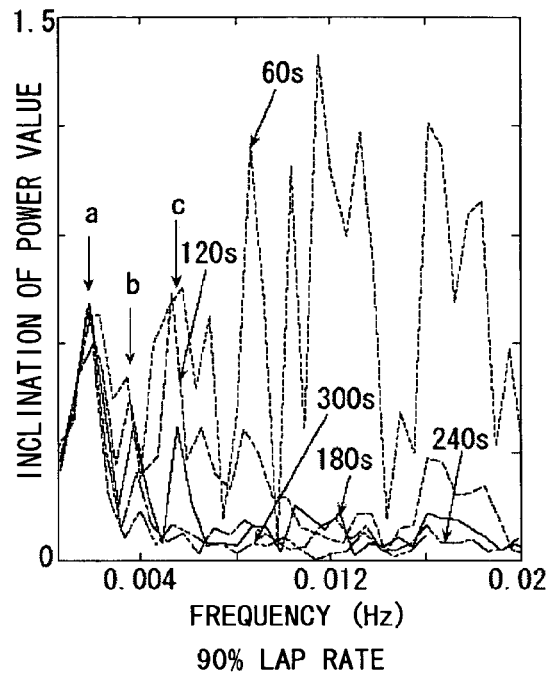
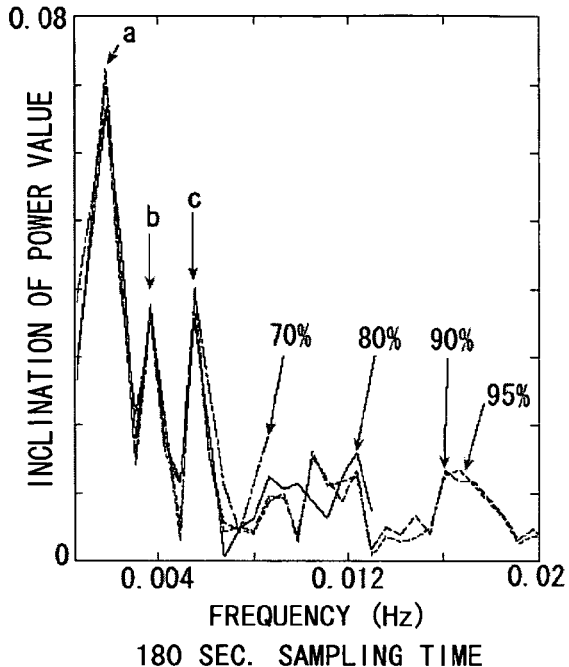
COMPARISON OF FREQUENCY ANALYSIS IN A CASE OF 30 MIN. EXPERIMENT
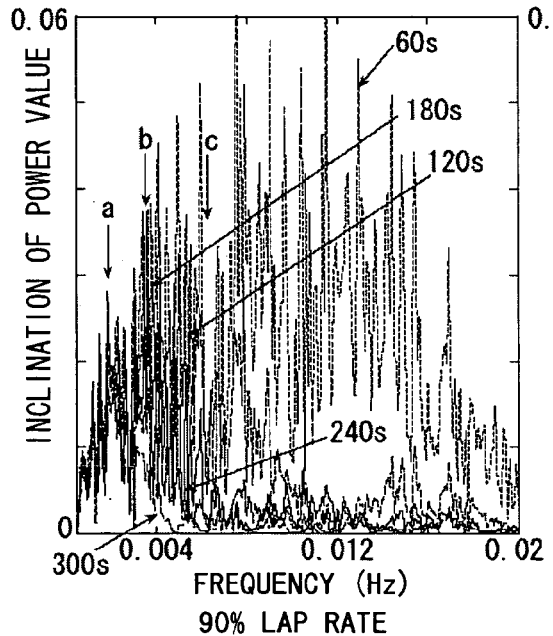
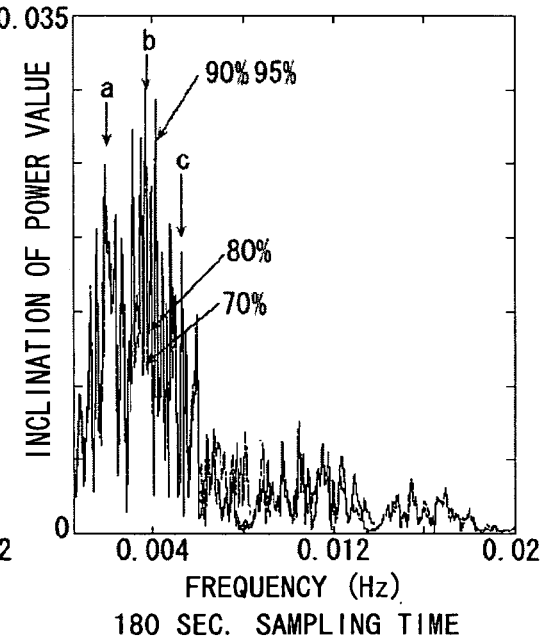
COMPARISON OF FREQUENCY ANALYSIS IN A CASE OF 180 MIN. EXPERIMENT

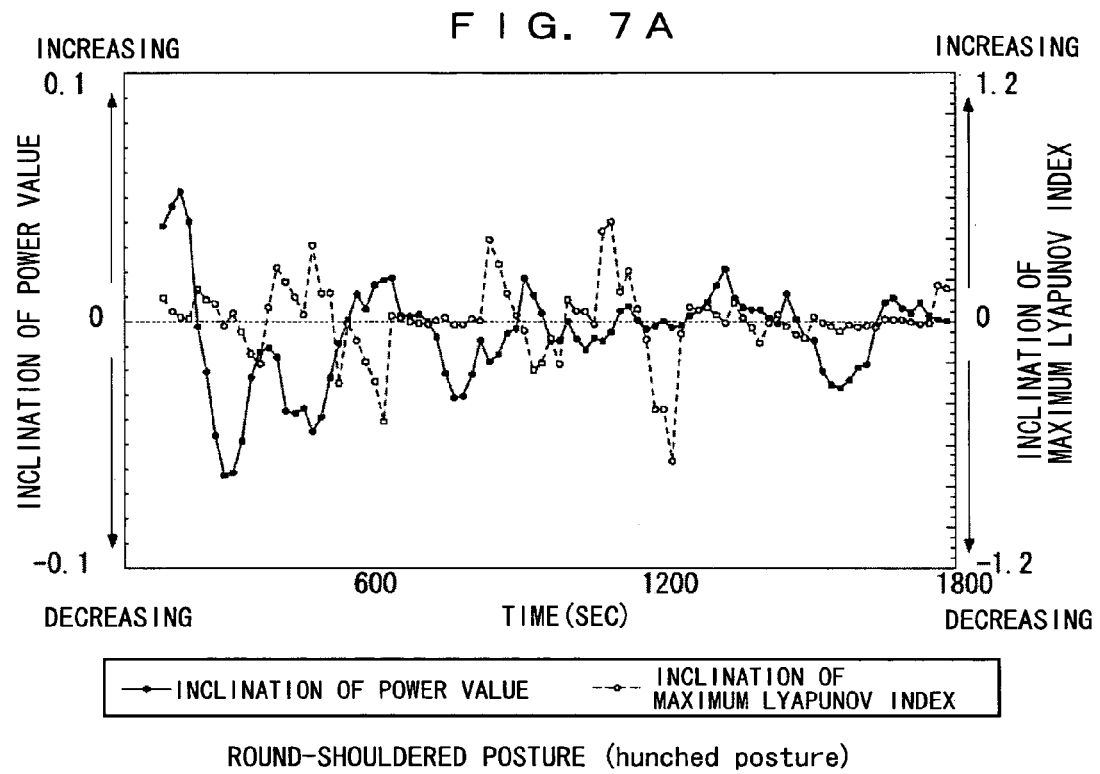
ROUND-SHOULDERED POSTURE (hunched posture)
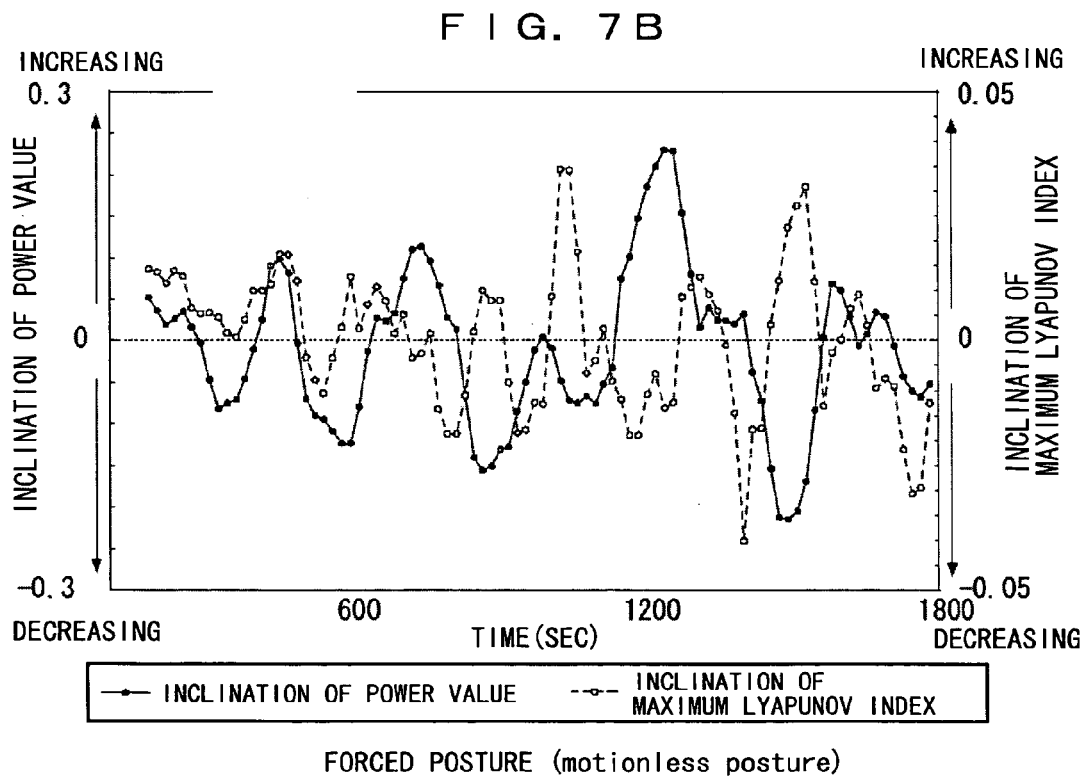
FORCED POSTURE (motionless posture)

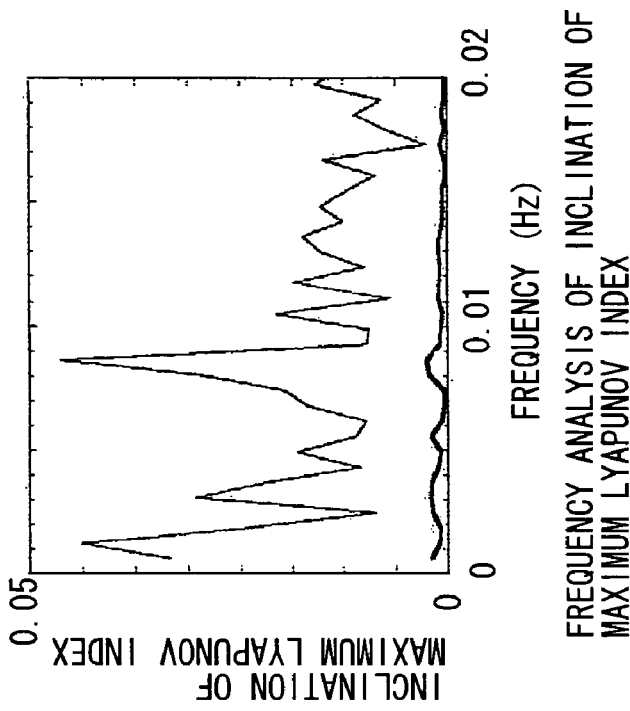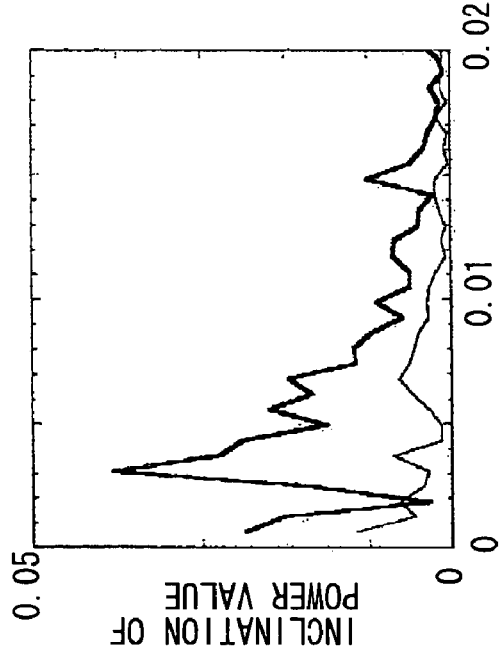

(0–30min.)
(30–60min.)
(60–90min.)
(90–120min.)
(120–150min.)
(150–180min.)
(SAMPLING TIME ZONE)

BODY PRESSURE DISPERSING TYPE SEAT
— INCLINATION OF POWER VALUE
— INCLINATION OF MAXIMUM LYAPUNOV INDEX

POSTURE-SUSTAINING TYPE SEAT

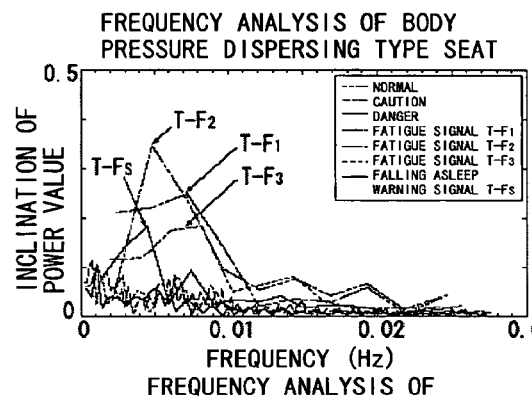

FIG. 10A
FREQUENCY ANALYSIS OF BODY PRESSURE DISPERSING TYPE SEAT

FREQUENCY ANALYSIS OF POWER VALUE INCLINATION

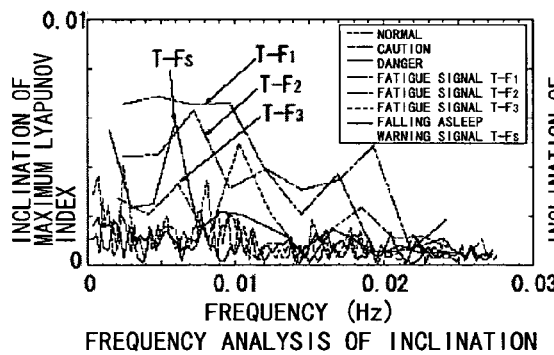

FREQUENCY ANALYSIS OF INCLINATION OF MAXIMUM LYAPUNOV INDEX

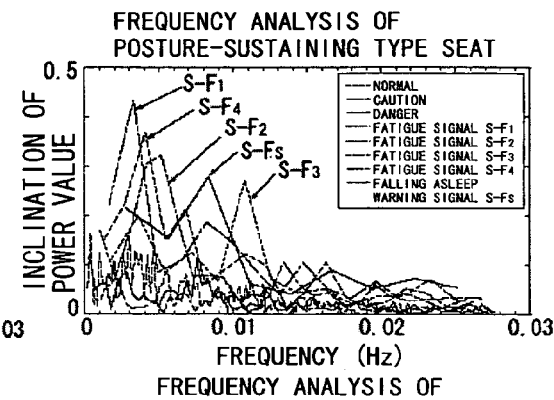

FIG. 10B
FREQUENCY ANALYSIS OF POSTURE-SUSTAINING TYPE SEAT

FREQUENCY ANALYSIS OF POWER VALUE INCLINATION

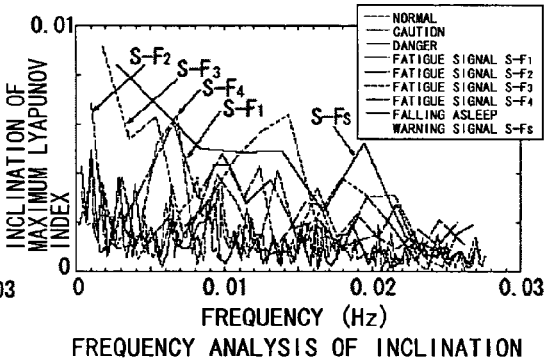

FREQUENCY ANALYSIS OF INCLINATION OF MAXIMUM LYAPUNOV INDEX

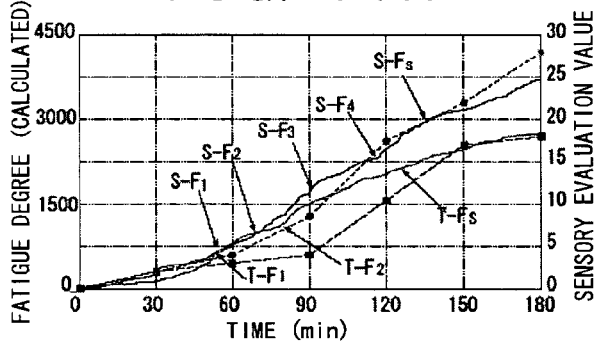

FIG. 11A

S-F: FATIGUE SIGNAL (POSTURE-SUSTAINING TYPE SEAT)
T-F: FATIGUE SIGNAL (BODY PRESSURE DISPERSING TYPE SEAT)

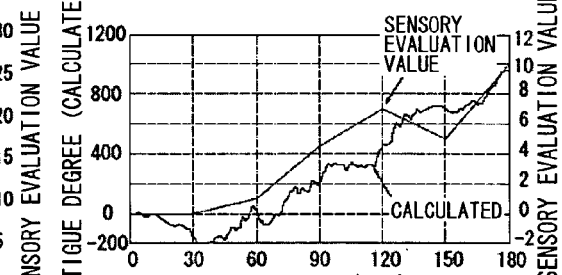

FIG. 11B

QUALITATIVE EVALUATION OF POSTURE-SUSTAINING TYPE SEAT ON THE BASIS OF BODY PRESSURE DISPERSING TYPE SEAT

— CALCULATED VALUE (POSTURE-SUSTAINING TYPE SEAT)
— CALCULATED VALUE (BODY PRESSURE DISPERSING TYPE SEAT)

-●- SENSORY EVALUATION VALUE (POSTURE-SUSTAINING TYPE SEAT)
-■- SENSORY EVALUATION VALUE (BODY PRESSURE DISPERSING TYPE SEAT)

(0-30min.)
(30-60min.)
(60-90min.)
(90-120min.)
(120-150min.)
(150-180min.)

BODY PRESSURE
DISPERSING TYPE SEAT (SAMPLING TIME ZONE)

— INCLINATION OF POWER VALUE
— INCLINATION OF MAXIMUM LYAPUNOV INDEX

POSTURE-SUSTAINING
TYPE SEAT

FIG. 13A

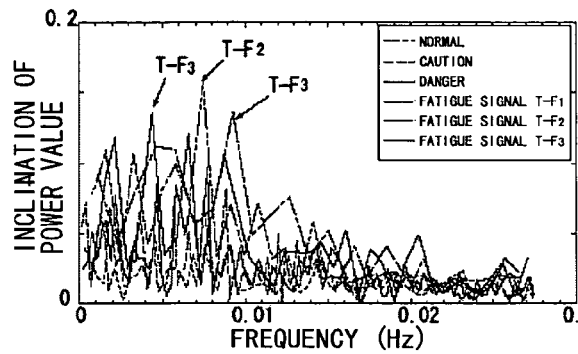

FREQUENCY ANALYSIS OF
POWER VALUE INCLINATION

FIG. 13B

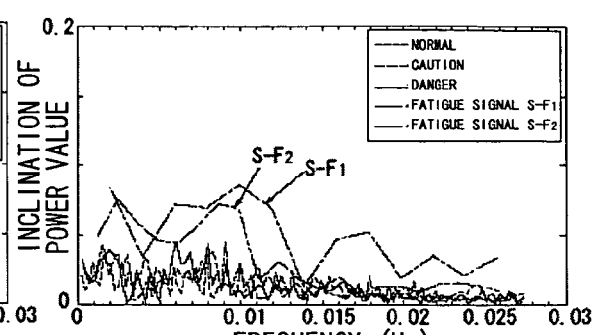

FREQUENCY ANALYSIS OF
POWER VALUE INCLINATION

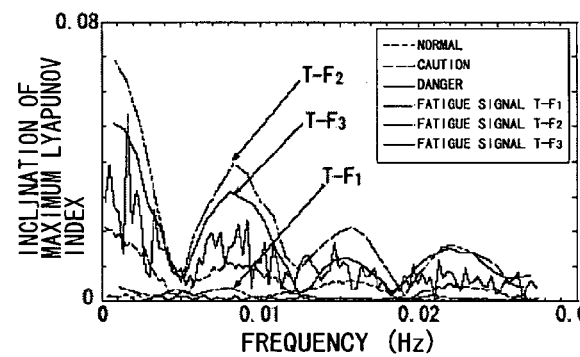

FREQUENCY ANALYSIS OF INCLINATION
OF MAXIMUM LYAPUNOV INDEX

FREQUENCY ANALYSIS OF BODY
PRESSURE DISPERSING TYPE SEAT

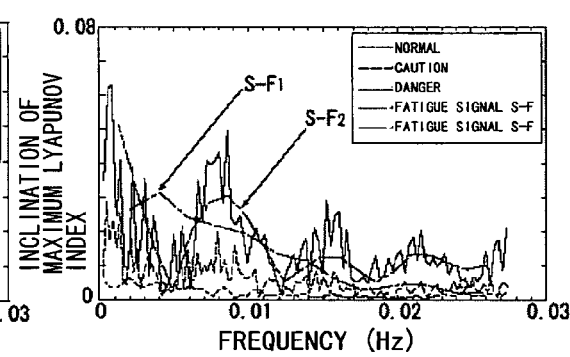

FREQUENCY ANALYSIS OF INCLINATION
OF MAXIMUM LYAPUNOV INDEX

FREQUENCY ANALYSIS OF
POSTURE-SUSTAINING TYPE SEAT

FIG. 14A

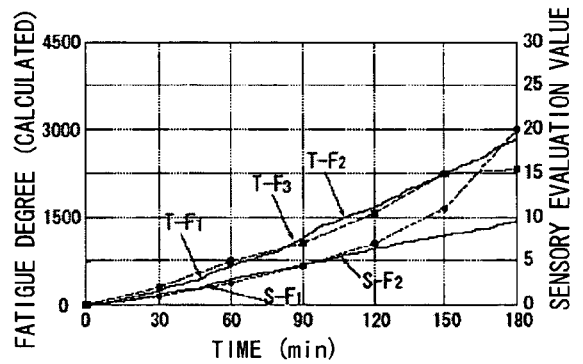

S-F: FATIGUE SIGNAL
(POSTURE-SUSTAINING TYPE SEAT)
T-F: FATIGUE SIGNAL
(BODY PRESSURE DISPERSING TYPE SEAT)

FIG. 14B

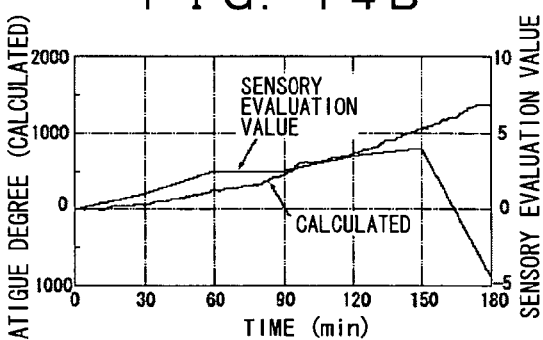

QUALITATIVE EVALUATION OF
POSTURE-SUSTAINING TYPE SEAT
ON THE BASIS OF BODY PRESSURE
DISPERSING TYPE SEAT

— CALCULATED VALUE (POSTURE-SUSTAINING TYPE SEAT)
— CALCULATED VALUE (BODY PRESSURE DISPERSING TYPE SEAT)

-●- SENSORY EVALUATION VALUE (POSTURE-SUSTAINING TYPE SEAT)
-■- SENSORY EVALUATION VALUE (BODY PRESSURE DISPERSING TYPE SEAT)

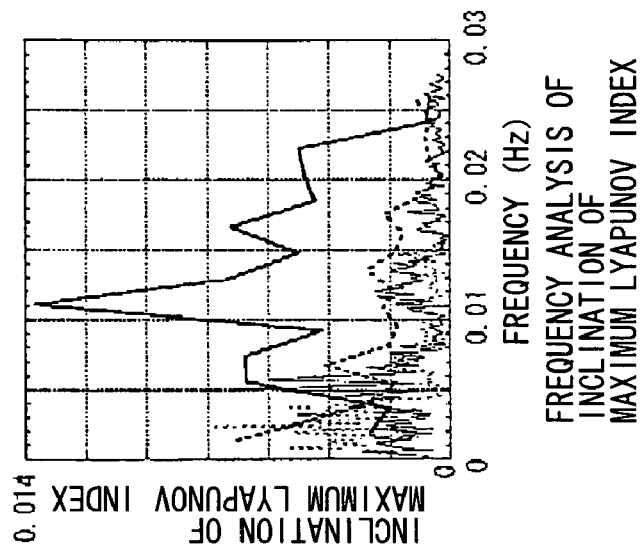
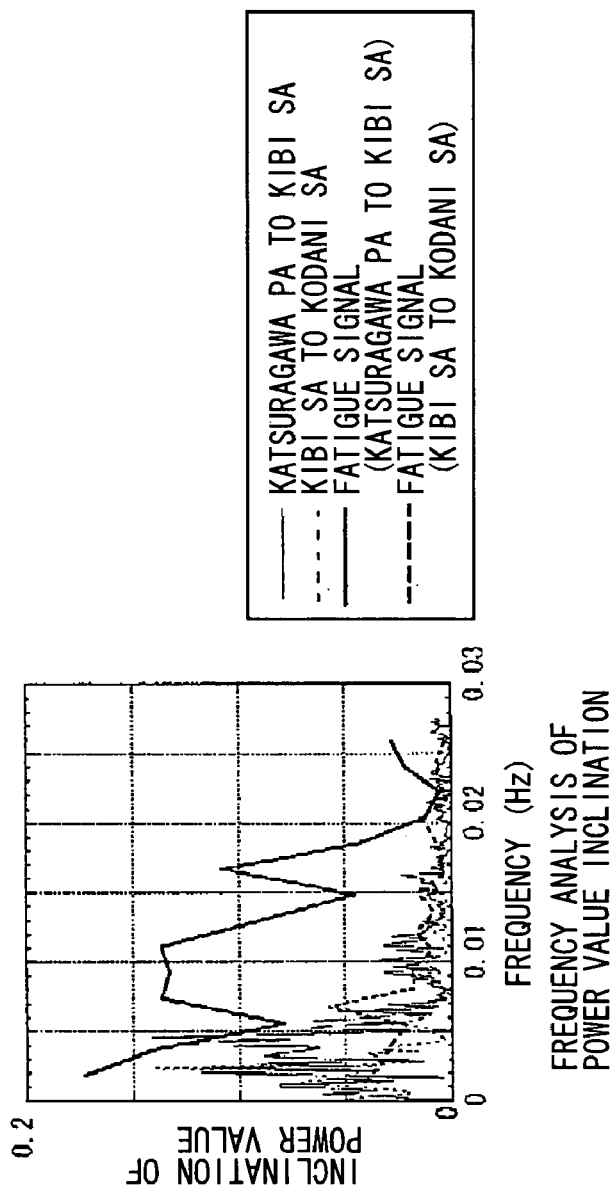
FIG. 16A
FIG. 16B

F I G. 2 0
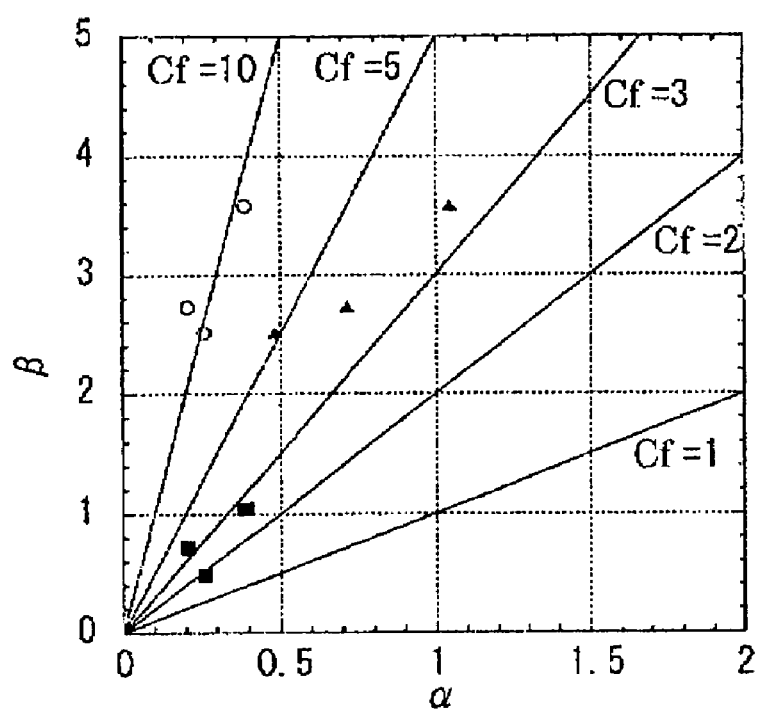
$$Cf = \frac{\alpha}{\beta}$$
| ○ | $\alpha$ = SLEEP SIGNAL, | $\beta$ = FALLING ASLEEP WARNING SIGNAL |
| ▲ | $\alpha$ = FATIGUE SIGNAL, | $\beta$ = FALLING ASLEEP WARNING SIGNAL |
| ■ | $\alpha$ = SLEEP SIGNAL, | $\beta$ = FATIGUE SIGNAL |

FIG. 21A

MUSCULAR TYPE TESTEE

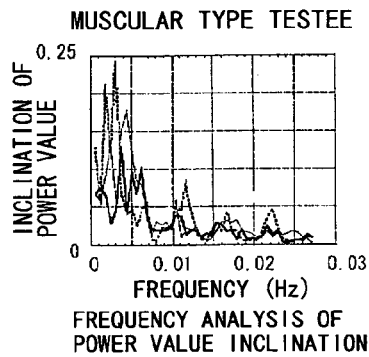

FREQUENCY ANALYSIS OF
POWER VALUE INCLINATION

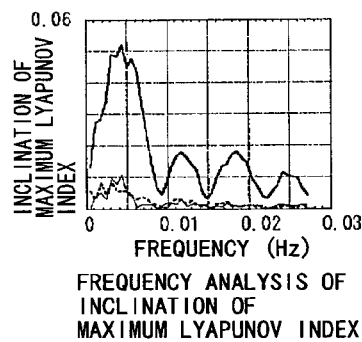

FREQUENCY ANALYSIS OF
INCLINATION OF
MAXIMUM LYAPUNOV INDEX

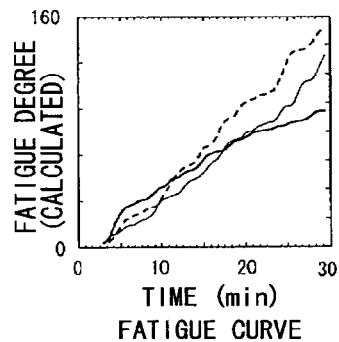

FATIGUE CURVE

FIG. 21B

LUMBAGO CARRYING TESTEE

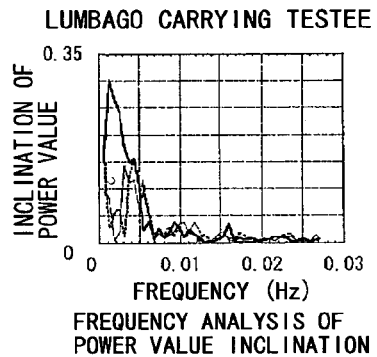

FREQUENCY ANALYSIS OF
POWER VALUE INCLINATION

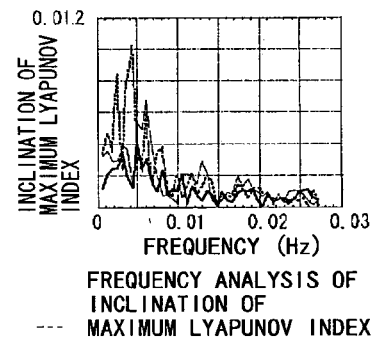

FREQUENCY ANALYSIS OF
INCLINATION OF
MAXIMUM LYAPUNOV INDEX

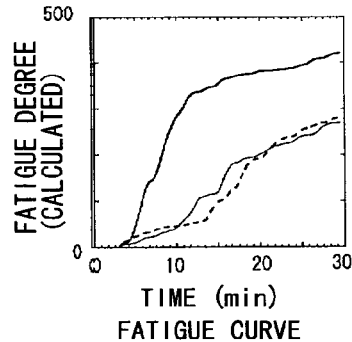

FATIGUE CURVE

FIG. 21C

LEPTOSOME TESTEE

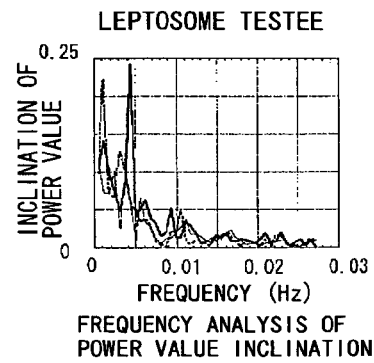

FREQUENCY ANALYSIS OF
POWER VALUE INCLINATION

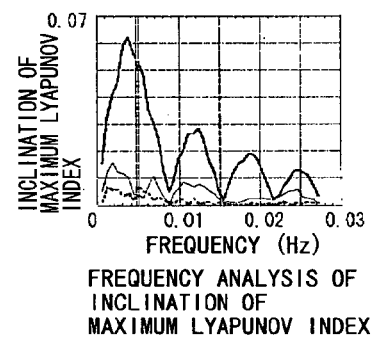

FREQUENCY ANALYSIS OF
INCLINATION OF
MAXIMUM LYAPUNOV INDEX

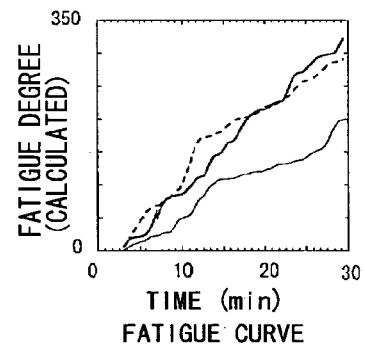

FATIGUE CURVE

——— NO BACK REST
——— NATURAL DRIVING POSTURE
----- STRESSING WAIST OVERHANG

FATIGUE DEGREE MEASUREMENT DEVICE, FATIGUE DETECTION DEVICE AND COMPUTER PROGRAM TO BE USED THEREIN

TECHNICAL FIELD

The present invention relates to a fatigue degree measurement device for quantitatively measuring human fatigue, a fatigue detection device for detecting the state of fatigue, and a computer program to be used for the above.

BACKGROUND ART

Detection of the state of a human living body, for instance, whether it is in an activation state (awakening state) or in a sleeping state is conventionally carried out by measuring a brain wave, and analyzing its brain wave pattern. However, measurement of a brain wave is required to perform in an environment to restrict usual behavior of a person such as attachment of brain wave electrodes or eye potentiometric electrodes on a head of a testee. Therefore, it is difficult to evaluate, for instance, the state of a living body during driving various transportation machines such as cars or trains without imposing a burden on a driver.

Whereas, monitoring the state of driver's living body (state of mind and body) during driving has been widely noticed as a safeguard against traffic accidents in recent years. For instance, in Patent Document 1 (Japanese Patent Application Laid-open No. Hei 9-308614) and Patent Document 2 (Japanese Patent Application Laid-open No. Hei 10-146321), a technology of monitoring the living body state using a heart beat or blood beat has been proposed. According to the technology disclosed in Patent Documents 1 and 2, it is possible to easily evaluate a living body state of a driver without installment of a large scale device for brain wave measurement on a head.

All of the devices disclosed in Patent Documents 1 and 2 calculate a chaos index of heart beats or blood beats, from which the state of mind and body of a driver is judged. Concretely, it is structured as follows. As one of the chaos indexes, Lyapunov index of heart beats or blood beats is determined, and when decrease in the Lyapunov index is seen during a prescribed period of time or longer in the time base change, it is determined that a stress load is generated in a level requiring a rest and a testee is in a state just before falling into a doze (the state of feeling drowsy). It has been already reported by Japanese Patent Application Laid-open No. Hei 4-208136 that a living body state could be objectively determined by the chaos index as a signal for a living body, and it may be possible to detect a state immediately before falling into a doze by a device disclosed in Patent Documents 1 and 2.

However, Patent Documents 1 and 2 only disclose that the technology treats measured heart beats or blood beats with only a chaos index such as Lyapunov index or the like, and detects a process from a change in decrease in Lyapunov index to a mentally stable state, and determines whether or not a fatigue state in such a degree of drowsiness is generated, but no trial has been made to grasp the degree of fatigue quantitatively.

Generally, as for a body force, there are vital body force relating to maintain a life, and an active body force with a background of the viable body force. The viable body force corresponds to a capability to maintain life and health, and is also called a defensive body force, while the active body force is a behavioral body force to move a body, and is generally taken as motility. The functions to support the behavioral body force include an energy generating system, an energy supplying system, and an energy control system. The energy generating system relates to a function to cause muscle fatigue of muscular strength, endurance, or the like, depending on the manner of muscular system workings. The energy supply system relates to a function of respiratory and circulatory system determined by oxygen intake or heart rate, and the energy control system relates to a function of agility, cooperativity, balancing ability, and flexibility. Therefore, as a consequence, physical burden can be determined from the state of the energy supply system, and mental burden from the state of the energy control system. From these judgment, an active state of the energy generation system which is a basis of muscle fatigue can be grasped.

The state of the above-described energy control system, namely, the conditions of mental burden can be grasped by determining Lyapunov index of living body signal data, and the state of the above-described energy supply system, namely, the state of physical burden can be grasped by measuring and treating force of resistance (referred to as "a power value" in the present specification) determined from a peak value in a cycle of the living body signal. In other words, an ACTH emission hormone is allowed to create various biological activities by a living body reaction called a general adaptation syndrome produced when various stressors are added to a living body. The force of resistance is a power which fights invasion and destruction from outside and includes such reactions as autonomic nervous system reactions shown by increase of heart rate caused by the reaction or increase in offensiveness, and results in consumption of energy and emission of calories. Accordingly, it is effective to determine the fatigue degree by detecting a decline in consumed calorie. In the present invention, such a force of resistance is determined from the peak value in a cycle of a living body signal, which is defined as a power value.

As for fatigue, there are peripheral fatigue and central fatigue. For instance, in the state of seated on a car seat for a long time, though there is an individual difference due to conditions of the seat or physical conditions, generally, the peripheral fatigue is predominant in the first half and the central fatigue is predominant in the latter half. As for the process of fatigue, a testee may begin to relax while calorie consumption is kept high and then calorie consumption declines, or calorie consumption may decline while a testee is excited, and then the testee relaxes to further lower calorie consumption. That is, a decline in consumed calorie commonly occurs in both fatigue, and it is conceived to be effective for grasping fatigue to analyze a power value from this point of view. However, conventionally, analysis of Lyapunov index is exclusively used to detect fatigue in the state of just before the onset of sleep from a mental burden, and since analysis of a power value is not taken into consideration, it is not suitable especially for detection of peripheral fatigue.

Furthermore, the values of Lyapunov index and heart beat in Patent Document 1 and 2 are taken in a time series change, but they are values for every 15 minutes or 30 minutes. Therefore, substantially real time state change necessary for monitoring during driving cannot be observed.

The present invention is achieved in consideration of the above-described problems, and an object of this invention is to provide a fatigue degree measurement device which can realize quantification of the degree of fatigue, can detect a fatigue signal irrespective of peripheral fatigue or central fatigue, and is suitable for measuring the degree of fatigue and detecting fatigue of, in particular, a driver, a fatigue detecting means, and computer programs.

DISCLOSURE OF THE INVENTION

In order to solve the above-described problems, the present invention described in claim 1 provides a fatigue degree measurement device, including:

a living body signal peak value detecting means for detecting the peak value in each cycle of an original waveform of the living body signal data collected b a living body signal measurement device;

a power value calculating means for calculating the difference between a peak value on the upper limit side and a peak value on the lower limit side for every prescribed time period from each peak value obtained by the living body signal peak value detecting means and for setting the difference as the power value;

a power value inclination calculating means for determining an inclination of the power values to the time base during the prescribed time period by slide calculating the prescribed times at a prescribed lap rate for the prescribed time period; and a fatigue degree calculating means for calculating an integral value by absolute value treatment of time base signal of power value inclination obtained from the slide calculation by the power value inclination calculating means to determine the obtained integral value as the degree of fatigue.

The present invention described in claim 2 provides the fatigue degree measurement device according to claim 1, in which the living body signal peak value detecting means is a means to perform smoothing differentiation of the living body signal data to determine the peak value on the upper limit side and the peak value on the lower limit side for the width fluctuation of the waveform with a predetermined threshold value.

The present invention described in claim 3 provides the fatigue degree measurement device according to claim 1, in which the power value calculating means is a means to calculate the difference between the mean value of the peak value on the upper limit side and the mean value of the peak value on the lower limit side within the prescribed time period range of the living body signal data as the power value.

The present invention described in claim 4 provides the fatigue degree measurement device according to claim 3, in which the power value calculating means is a mean to calculate the square value of the difference between the mean value of the peak value on the upper limit side and the mean value of the peak value on the lower limit side within the prescribed time period range of the living body signal data as the power value.

The present invention described in claim 5 provides the fatigue degree measurement device according to claim 1, in which the time interval used in the slide calculation in the power value inclination calculating means is 180 seconds and the lap rate is 90%.

The present invention described in claim 6 provides the fatigue degree measurement device according to claim 1, further including:

a maximum Lyapunov index calculating means for calculating the maximum Lyapunov index by chaos analyzing the living body signal data;

a maximum Lyapunov index peak value detecting means for detecting the peak value in each cycle of a time series change waveform of the calculated maximum Lyapunov index;

a maximum Lyapunov index inclination calculating means for determining an inclination of each peak value of the maximum Lyapunov indexes obtained by the maximum Lyapunov index peak value detecting means to the time base during the prescribed time period by slide calculating the prescribed times at a prescribed lap rate for the prescribed time period, in addition to the inclination of the power value; and a comparing and determining means for determining as the generating point of a fatigue signal when the inclination of the power value obtained by slide calculating using the power value inclination calculating means and the maximum Lyapunov index obtained by slide calculating using the maximum Lyapunov index inclination calculating means stably show the phase difference of substantially 180° among time series signals.

The present invention described in claim 7 provides the fatigue degree measurement device according to claim 6, in which the maximum Lyapunov index peak value detecting means is a means to perform smoothing differentiation of the time series change waveform of the maximum Lyapunov index to determine the peak value on the upper limit side and the peak value on the lower limit side for the width fluctuation of the waveform with a predetermined threshold value.

The present invention described in claim 8 provides the fatigue degree measurement device according to claim 6, in which the time interval used in the slide calculation in the maximum Lyapunov index inclination calculating means is 180 seconds and the lap rate is 90%.

The present invention described in claim 9 provides a fatigue detection device, including:

a living body signal peak value detecting means for detecting the peak value in each cycle of an original waveform of the living body signal data collected by a living body signal measurement device;

a power value calculating means for calculating the difference between a peak value on the upper limit side and a peak value on the lower limit side for every prescribed time period from each peak value obtained by the living body signal peak value detecting means and for setting the difference as the power value;

a power value inclination calculating means for determining an inclination of the power values to the time base during the prescribed time period by slide calculating the prescribed times at a prescribed lap rate for the prescribed time period;

a maximum Lyapunov index calculating means for calculating the maximum Lyapunov index by chaos analyzing the living body signal data;

a maximum Lyapunov index peak value detecting means for detecting the peak value in each cycle of a time series change waveform of the calculated maximum Lyapunov index;

a maximum Lyapunov index inclination calculating means for determining an inclination of each peak value of the maximum Lyapunov indexes obtained by the maximum Lyapunov index peak value detecting means to the time base during the prescribed time period by slide calculating the prescribed times at a prescribed lap rate for the prescribed time period; and a comparing and determining means for determining as the generating point of a fatigue signal when the inclination of the power value obtained by slide calculating using the power value inclination calculating means and the maximum Lyapunov index obtained by slide calculating using the maximum Lyapunov index inclination calculating means stably show the phase difference of substantially 180° among time series signals.

The present invention described in claim 10 provides the fatigue detection device according to claim 9, in which the living body signal peak value detecting means is a means to perform smoothing differentiation of the living body signal data to determine the peak value on the upper limit side and the peak value on the lower limit side for the width fluctuation of the waveform with a predetermined threshold value, and the maximum Lyapunov index peak value detecting means is a means to perform smoothing differentiation of the time series change waveform of the maximum Lyapunov index to determine the peak value on the upper limit side and the peak value on the lower limit side for the width fluctuation of the waveform with a predetermined threshold value.

The present invention described in claim 11 provides the fatigue detection measurement device according to claim 9, in which the time interval used in the slide calculation in the power value inclination calculating means and the maximum Lyapunov index inclination calculating means is 180 seconds and the lap rate is 90%.

The present invention described in claim 12 provides the fatigue detection device according to claim 9, in which the comparing and determining means includes a fatigue state determining means for determining the state of fatigue based on the inclinations of power value and the maximum Lyapunov index appearing in time series.

The present invention described in claim 13 provides the fatigue detection device according to claim 12, in which the fatigue state determining means includes a means for performing frequency analysis of the change in the inclinations of power value and the maximum Lyapunov index appearing in time series, and determining a central fatigue predominant state when power spectrum of the inclination of the maximum Lyapunov index is large, and a peripheral fatigue predominant state when the power spectrum of the inclination of the power value is large.

The present invention described in claim 14 provides a computer program to make a computer execute a process to measure the degree of fatigue by analyzing living body signal data collected by a living body signal measurement device to measure a human living body signal, including:

a living body signal peak value detecting step of detecting the each cycle peak value of the original waveform of the living body signal data;

a power value calculating step of calculating the difference between a peak value on the upper limit side and a peak value on the lower limit side for every prescribed time period from each peak value obtained from the living body signal peak value detecting step to set the difference as the power value;

a power value inclination calculating step of determining the inclination of the power value to the time base during the prescribed time period by slide calculating the prescribed times at a prescribed lap rate for the prescribed time period; and a fatigue degree calculating step of calculating an integral value by absolute value treatment of the time base signal of the power value inclination obtained from slide calculation by the power value inclination calculating step to determine the obtained integral value as the degree of fatigue.

The present invention described in claim 15 provides a computer program to make a computer execute a process to detect fatigue by analyzing living body signal data collected by a living body signal measurement device to measure a human living body signal, including:

a living body signal peak value detecting step of detecting the peak value in each cycle of the original waveform of the living body signal data collected by a living body signal measurement device;

a power value calculating step of calculating the difference between a peak value on the upper limit side and a peak value on the lower limit side for every prescribed time period from each peak value obtained from the living body signal peak value detecting means to set the difference as the power value;

a power value inclination calculating step of determining the inclination of the power value to the time base during the prescribed time period by slide calculating the prescribed times at a prescribed lap rate for the prescribed time period;

a maximum Lyapunov index calculating step of calculating the maximum Lyapunov index by chaos analyzing the living body signal data;

a maximum Lyapunov index peak value detecting step of detecting the peak value in each cycle of a time series change waveform of the calculated maximum Lyapunov index;

a maximum Lyapunov index inclination calculating step of determining the inclination of each peak value of the maximum Lyapunov indexes obtained by the maximum Lyapunov index peak value detecting step to the time base during the prescribed time period by slide calculating the prescribed times at a prescribed lap rate for the prescribed time period, and a comparing and determining step of determining as the generating point of a fatigue signal when inclination of the power value obtained by slide calculating using the power value inclination calculating step and the maximum Lyapunov index obtained by slide calculation using the maximum Lyapunov index inclination calculating step stably show the phase difference of substantially 180° among time series signals.

The present invention described in claim 16 provides the computer program according to claim 15, in which the comparing and determining step includes a fatigue state determining step to perform frequency analysis of the change in inclination of the power value and of the maximum Lyapunov index appearing in time series, and determines to be a central fatigue predominant state when the power spectrum of the inclination of the maximum Lyapunov index is large, and to be a peripheral fatigue predominant state when the power spectrum of the inclination of the power value is large.

EFFECT OF THE INVENTION

The fatigue degree measurement device and the computer programs of the present invention are structured including a living body signal peak value detecting means to detect peak values of respective cycles in the original waveform of living body signal data, a power value calculating means for calculating the difference between a peak value on the upper limit side and a peak value on the lower limit side for every prescribed time period from each peak value obtained by the living body signal peak value detecting means and for setting the difference as the power value and a power value inclination calculating means to determine the inclination of the power values, to calculate an integral value by absolute value treatment of the time series signals of the inclination of the power values to determine the integral value as the degree of fatigue. As a result, it becomes possible to realize quantification of a human fatigue degree.

Moreover, the fatigue degree measurement device and the computer programs of the present invention can detect fatigue signals by making a structure including a maximum Lyapunov index inclination calculating means for determining the inclination to the time base of the maximum Lyapunov indexes in addition to the structure calculating the inclination of the power values. Moreover, it is possible to determine the kind of fatigue corresponding to the appeared fatigue signal by the comparison and determining means.

BRIEF DESCRIPTION OF THE DRAWINGS

FIGS. 3A to 3E are views showing the inclinations of power value and the maximum Lyapunov index when time of sampling is varied to perform the most suited calculation of inclination in a sleeping experiment. FIG. 3F is a view showing its wave height coefficient;

FIG. 5A is a view showing the result of frequency analysis shown in FIGS. 3A to 3E, and FIG. 5B is a view showing the result of frequency analysis shown in FIGS. 4A to 4D;

FIGS. 6A and 6B are views showing the result of frequency analysis on the inclinations of the power value and the maximum Lyapunov index obtained by a sleeping experiment for 180 min. FIG. 6A shows a case taking the slide lap rate 90% and changing the sampling time, while FIG. 6B is a case taking the sampling time for 180 sec and changing the slide lap rate;

FIGS. 7A and 7B are views showing a time series change of the inclinations of the power value and the maximum Lyapunov index for 30 min. obtained during a short time seating experiment. FIG. 7A is a view showing data when a testee is seated in a round-shouldered posture, while FIG. 7B is a view showing data when the testee is seated in a forced posture on the same seat;

FIGS. 8A and 8B are views showing the result of frequency analysis in the round-shouldered posture and forced posture in FIGS. 7A and 7B;

FIG. 9A is a view showing a case of seated on a body pressure dispersing type seat, while FIG. 9B is a view showing a case of seated on a posture-sustaining type seat;

FIG. 10A is a view showing the result of frequency analysis of the body pressure dispersing type seat in FIG. 9A, and FIG. 10B is a view showing the result of frequency analysis of the posture-sustaining type seat in FIG. 9B;

FIG. 11A is a view showing data calculated as an integral value taken by absolute value treatment of time series signals of the power value inclination for respective fatigue degrees of the body pressure dispersing type seat in FIG. 9A and the posture-sustaining type seat in FIG. 9B. FIG. 11B is a view showing the fatigue curve evaluating the posture-sustaining type seat with respect to the body pressure dispersing type seat;

FIG. 12A is a view showing a case of seated on a body pressure dispersing type seat, while FIG. 12B is a view showing a case of seated on a posture-sustaining type seat;

FIG. 13A is a view showing the result of frequency analysis of the body pressure dispersing type seat in FIG. 12A, and FIG. 13B is a view showing the result of frequency analysis of the posture-sustaining type seat in FIG. 12B;

FIG. 14A is a view showing data calculated as an integral value taken by absolute value treatment of time series signals of the power value inclination for respective fatigue degrees of the body pressure dispersing type seat in FIG. 12A and the posture-sustaining type seat in FIG. 12B. FIG. 14B is a view showing the fatigue curve evaluating the fatigue degree (calculated value) and sensory evaluation value of the body pressure dispersing type seat with respect to the posture-sustaining type seat;

FIGS. 16A and 16B are views showing a result of frequency analysis in FIGS. 15A and 15B;

FIG. 19A shows the fatigue curve of a testee in the driver's seat, FIG. 19B shows the fatigue curve of a testee in the passenger seat, and FIG. 19C shows a view in which both fatigue curves are overlapped;

FIG. 20 is a view comparing the wave height coefficients of falling asleep warning signals, fatigue signals, and sleeping signals by the vehicle driving experiments; and FIGS. 21A to 21C are views showing frequency analysis of the inclinations of power values and the maximum Lyapunov indexes and fatigue curves in a lumbago acceleration short time seating experiment, and FIG. 21A shows data of a muscular testee, FIG. 21B shows data of a testee suffering lumbago, and FIG. 21C shows data of a leptosome testee.

BEST MODE FOR CARRYING OUT THE INVENTION

Figure 1:
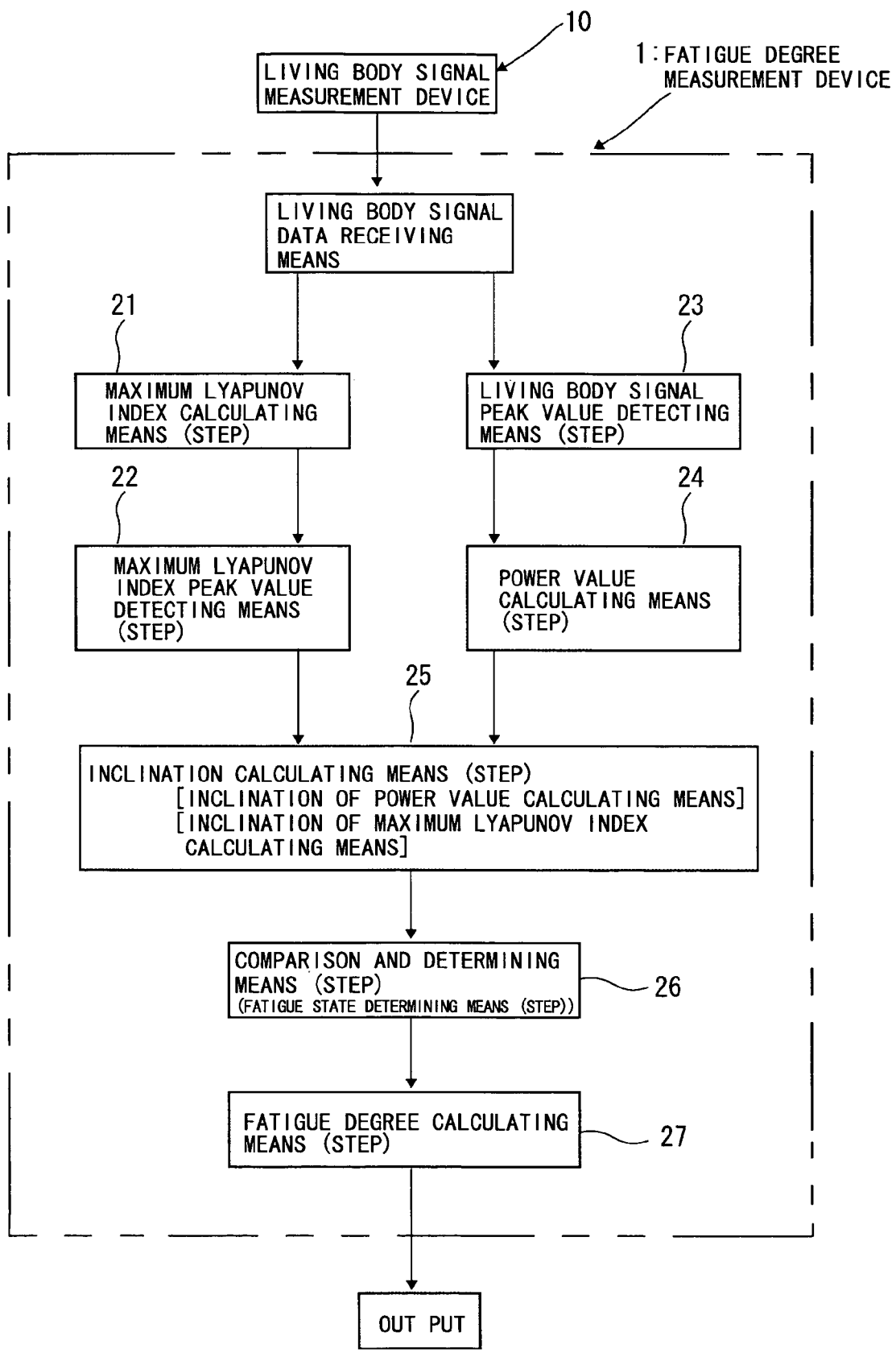
FIG. 1 is a block diagram showing a configuration of a fatigue degree measurement device according to an embodiment of the present invention.

Hereinafter, the present invention will be explained further in detail according to an embodiment shown in the drawings. FIG. 1 is a block diagram of a fatigue degree measurement device 1 according to an embodiment of the present invention. As shown in FIG. 1, the fatigue degree measurement device 1 of the present embodiment receives living body signal data collected from a living body signal measurement device 10 and carries out a prescribed analysis treatment.

Although any living body signal measurement device 10 can be used so far as it can collect living body signals such as pulse waves, heart beats, or the like, it is preferable to use a device which can observe the state of peripheral circulatory systems such as a finger tip volume pulse wave or the like. As a measurement device for a finger tip volume pulse wave, for instance, a device having an infrared light-emitting diode and a phototransistor placed on a finger for measurement can be used. When, for instance, a living body signal of a person who is seated on a driver's seat of a car or a train is sensed, it is possible to use a device provided with a pressure sensor attached to a seat back or a seat cushion of a driver's seat, and to detect a pulse wave from a pressure value change. In this case, it is necessary not to let a person feel a feeling of something foreign during seating, and preferably, for instance, a film-shaped piezoelectric element is used as a pressure sensor, which is stuck on the surface of a seat back or seat cushion.

The fatigue degree measurement device 1 is provided with a receiver to receive a living body signal data collected by the living body signal measuring device 10, and includes a maximum Lyapunov index calculating means (maximum Lyapunov index calculating step) 21, a maximum Lyapunov index peak value detecting means (maximum Lyapunov index peak value detecting step) 22, a living body signal peak value detecting means (living body signal peak value detecting step) 23, a power value calculating means (power value calculating step) 24, an inclination calculating means (inclination calculating step) 25, a comparing and determining means (comparing and determining step) 26, and a fatigue degree calculating means (fatigue degree calculating step) 27.

Figure 2:
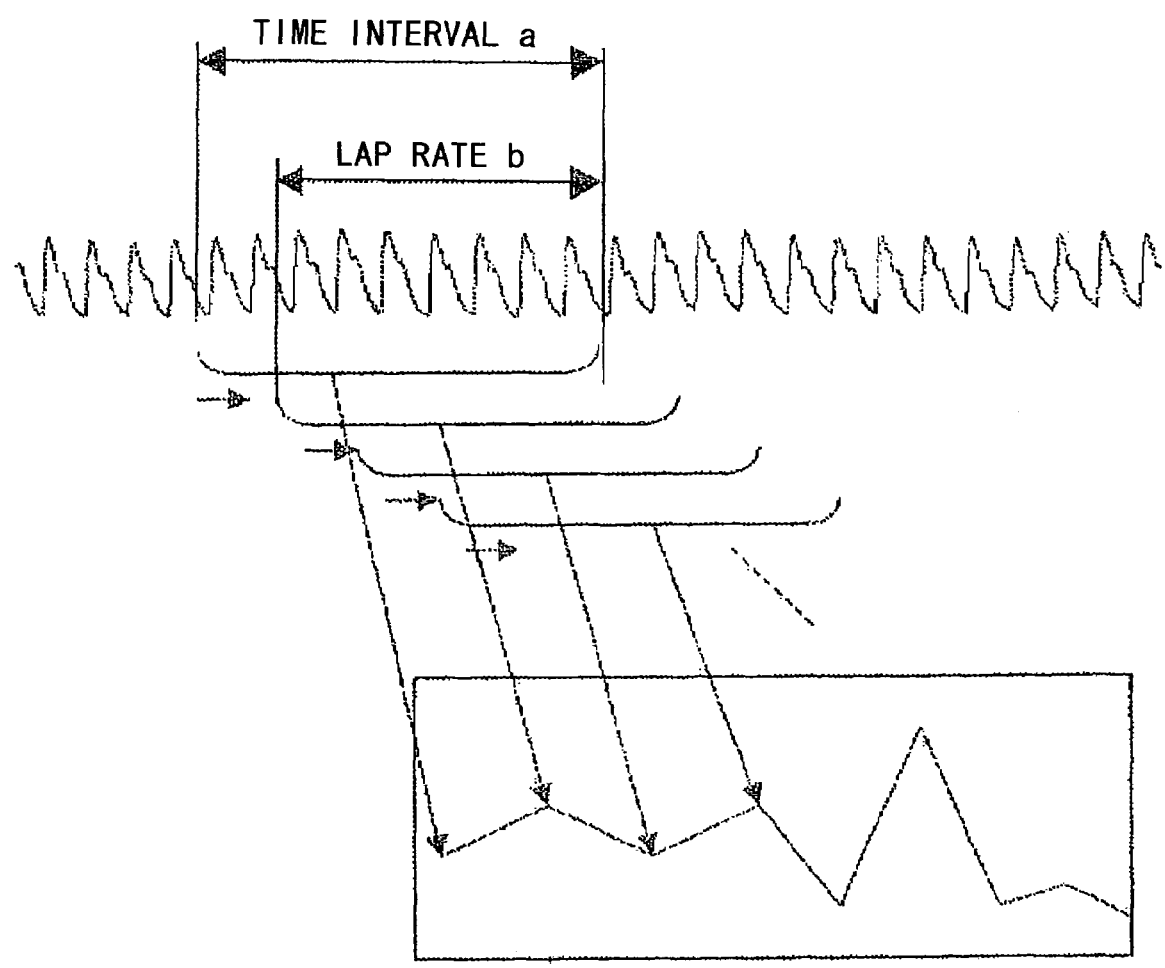
FIG. 2 is a view to explain a technique of slide calculation.

The maximum Lyapunov index is one of chaos indexes, and is a value showing a degree of initial value dependency of chaos by means of an index, which is an amount showing a degree in which a distance between two neighboring orbits among orbits drawn by a chaos atractor is increasing accompanied by passage of time. More concretely, the living body signal data collected from the living body signal measurement device 10 are firstly converted to time series signals of the living body signals (for instance, finger-tip volume pulse wave) by a maximum Lyapunov index calculating means (maximum Lyapunov index calculating step) 21 to reform the time series signals in a state space by a time-delay method. A time series delay time of the pulse wave is 50 ms, and if embedded dimensions are expressed by FNN (False Near Neighbors) method, since FNN is nearly zero at dimension 3, and absolutely zero at dimension 4, the best suited embedded dimension is set as 4 dimension. The Lyapunov indexes are numerically expressed to the obtained consecutive data calculation values, by slide calculation shown in FIG. 2, using sliding window approach at 30 seconds. Values of the maximum Lyapunov index among the Lyapunov indexes are plotted at every one second, and the time series data of the maximum Lyapunov indexes are calculated. Next, in the inclination calculation means 25, the slide calculation shown in FIG. 2 is performed to time series data of the maximum Lyapunov indexes, which will be described in detail later.

The maximum Lyapunov index peak value detecting means (maximum Lyapunov index peak value detecting step) 22 of the present embodiment detects each waveform cycle peak value of time series change of the maximum Lyapunov indexes calculated as above. Concretely, the maximum Lyapunov indexes calculated as above is smoothed through smoothing differentiation by Savitzky and Golay, and the peak values on the upper limit side and the peak values (bottom values) on the lower side are seated. In a primary differentiation waveform using smoothing with a prescribed threshold value, preferably with 70% of the fluctuation width of the waveform as a threshold value, differentiation value=0 is taken as each peak value. By smoothing through smoothing differentiation, the effect of noise can be reduced.

The living body signal peak value detecting means (living body signal peak value detecting step) 23 detects each cycle peak value of original waveform of the living body signal data obtained by the living body signal measurement device 10. Concretely, the living body signal data is smoothing differentiated by Savitzky and Golay, detection is made with a prescribed threshold value, preferably with 70% of the fluctuation width of the waveform as a threshold value, and the peak values on the upper limit side and the peak values (bottom values) on the lower side are determined.

In the power value calculating means (power value calculating step) 24, each peak value of the living body signal data obtained by the living body signal peak value detecting means 23 is divided for every prescribed time period previously established, for instance, for every 5 seconds (s), to determine the average values of the upper limit side peak values and the lower limit side peak values, and differences between these average values are determined as power values. Note that, in the present embodiment, the power value is determined by squaring the difference between the average value of the upper limit side peak value and the average value of the lower limit side peak value.

The inclination calculating means (inclination calculating step) 25 includes a maximum Lyapunov index inclination calculating means (maximum Lyapunov index inclination calculating step) and a power value inclination calculating means (power value inclination calculating step). The maximum Lyapunov index inclination calculating means determines by slide calculating an inclination in the time base during the prescribed time period of each peak value of the maximum Lyapunov index obtained by the maximum Lyapunov index peak value detecting means 22 for the prescribed time period and the prescribed times at a prescribed lap rate. The power value inclination calculating means determines by slide calculating an inclination in the time base during the prescribed time period of the power value obtained by the power value calculating means 24 at a prescribed lap rate the prescribed times (refer to FIG. 2). The slide calculation can be performed as follows.

For instance, when an inclination for T seconds (s) is determined at a slide lap rate 90%, firstly, the peak value of the maximum Lyapunov indexes during 0 (s) to T (s), and the inclination to a power value in the time base is determined by a least-square approximation method. Then, respective inclinations in the following equations are determined by the least-squares approximation method, during T/10 (s) to T+T/10 (s),      slide calculation (1):

during 2×T/10 (s) to T+2×T/10 (s),      slide calculation (2):

during n×T/10 (s) to T+n×T/10 (s).      slide calculation (n):

In order to grasp the characteristics of the maximum Lyapunov indexes and the power values during a certain time period broadly, 180 seconds is the best suited for the sampling time interval (T seconds) at the time of a slide calculation, and 90% of the slide lap rate is best suited. The results are obtained from sleeping experiments for 30 minutes under the same conditions for several testees, collecting and analyzing finger-tip volume pulse waves. FIGS. 3A to 5B show one of the examples.

FIGS. 3A to 3E show the inclinations of the maximum Lyapunov indexes and the inclinations of the power values, by taking the sampling time intervals for the inclination calculation as 60 seconds, 120 seconds, 180 seconds, 240 seconds, and 300 seconds, and by taking the slide lap rate at a unified value of 90%. FIG. 5A shows the results of frequency analysis. Note that, in the drawing, "a" denotes the amplitude of the falling asleep warning signal, "b" denotes the amplitude of signals in transition from the appearance of the falling asleep warning signal to sleep, and "c" denotes the amplitude of the sleeping signal during sleep.

In each case, a wave height coefficient of a discrete signal of inclination: Cf=Xp/Xs (where Xp shows a maximum amplitude of the indication signal, Xs shows an amplitude of a signal in a steady state before or after generating the indication signal) is determined from time series signals of respective indication signals (here, falling asleep warning signal a, transition state signal b, and sleeping signal c), and a condition under which characteristics of the inclination appear in a best sensitivity is determined from the above-described value. The results are shown in FIG. 3F. From this drawing, it is understood that 180 seconds is most sensitive as a time interval to calculate the inclination. The reason to establish a center value at 180 seconds is because emission frequency of command in the muscle activity due to fatigue is carried mainly by the peripheral reflection mechanism in the muscle. In other words, it is thought that it is related to the fact that though the command in the muscle activity is reduced due to attenuation of excitability in the upper level central nervous system and participation of peripheral restrictive reflection mechanism, the central excitation level is restored in 180 seconds when the bloodstream returns to normal.

Figure 4A:
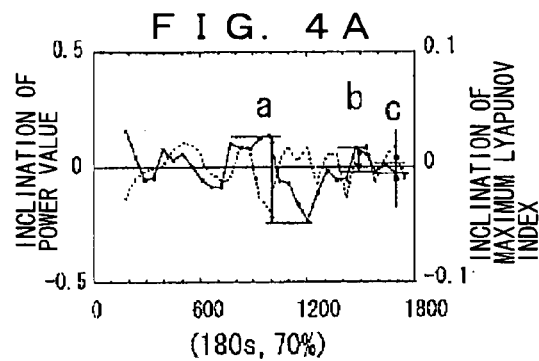
FIGS. 4A to 4D are views showing the inclinations of the power value and the maximum Lyapunov index when a slide lap rate is varied to perform the most suited calculation of inclination in a sleeping experiment for 30 min.
Figure 4B:
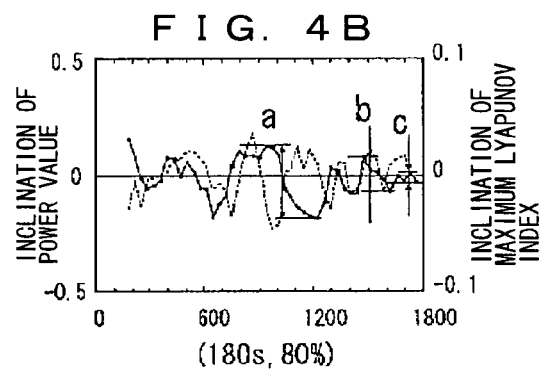
Figure 4C:
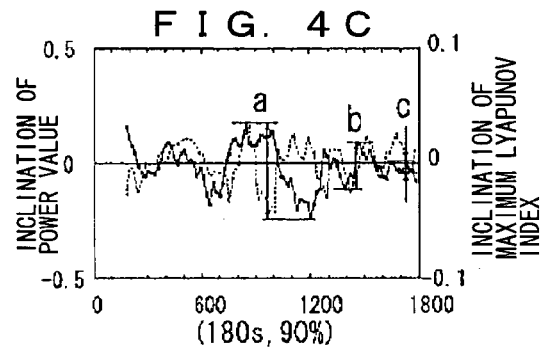
Figure 4D:
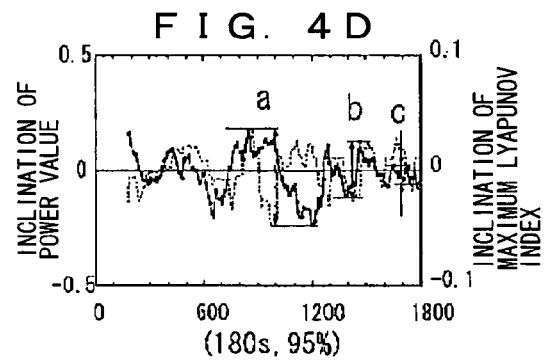
Figure 4E:
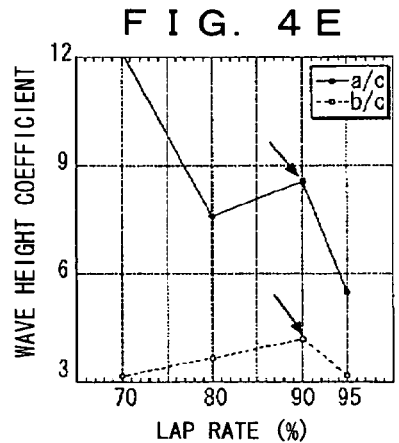
FIG. 4E is a view showing its wave height coefficient.

Whereas, the slide lap rate is calculated from 70% to 95% in the case of sampling time interval 180 seconds. As for less than 70% of the slide lap rate, since the time series signals become less frequently, the calculation is omitted. FIGS. 4A to 4D show the result, and FIG. 5B shows the frequency analysis result. From these drawings, it is found that noise is low when the slide lap rates are at 90% and 95%, but when a graph in FIG. 4E showing the wave height coefficient is referred, the sensitivity is the highest at 90% of the slide lap rate. From this fact, time interval 180 seconds and slide lap rate 90% which can pick up the indication signals a, b, c clearly are most preferable conditions for extracting suitable information.

Note that the above-described result is for the case of experiment time 30 min., whereas in the case of experiment time 180 min, as shown in FIGS. 6A and 6B, the indication signals a, b, c can remarkably extract the characteristics when 180 seconds time interval and 90% slide lap rate are used.

From these results, in the inclination calculating means 25, the best way to determine the inclination is to determine the rate of change of the maximum Lyapunov indexes for 180 seconds and the rate of change of the power values for 180 seconds by the least-squares method, and to determine the inclination for 180 seconds with 18 seconds thereafter as a starting point by the least-squares method.

As frequency bands of the circulatory living body signal are concentrated on the frequency band at 10 Hz or less. They are 0.25 to 0.33 Hz for breathing, 0.83 to 1.17 Hz for heart beat, and 0.5 to 10 Hz for pulse wave. In the conventional pulse wave analysis, information such as hardness of the blood vessel, blood viscosity, and the like is obtained from analysis from the wave form pattern of the pulse wave, and noise having the frequency band at 10 Hz or more is treated by providing a low pass filter. However, it is difficult to control an effect caused by mixing of noise having a frequency band at 10 Hz or less, and a site to collect pulse wave analysis is limited. On the other hand, a finger-tip volume pulse wave collected in a car or in an environment where body movement occurs is generally vibration excited by an irregular vibration source, and it is not practical to detect the degree of driver fatigue if the effect of noise under an irregular vibration source is not reduced. However, the above-described treatment is carried out, and by establishing a structure to grasp a broad trend change of the inclinations of the power values and maximum Lyapunov indexes, the effect of noise can be reduced.

In other words, it is possible to prevent mixing of noise, and to precisely collect the low frequency fluctuation by a method of determining the differential coefficients (inclination) of the maximum Lyapunov indexes and power values of original waveform of the living body signals such as finger-tip volume pulse wave or the like by performing slide calculation a number of times.

The comparing and determining means (comparing and determining step) 26 compares the inclination of the power values obtained by the inclination calculating means 25 with the inclination of the peak values in the maximum Lyapunov indexes to determine the appearance of a fatigue signal. Whether it is a fatigue signal or not is determined by recognizing the appearance of characteristic signal group stably showing a phase difference of about 180° (opposite phase) between both among the time series signals when the inclinations of the power values and maximum Lyapunov indexes are plotted on the time base of the same graph from later-described test result. The time when such a characteristic signal group appears in a later-described test is consistent with a timing which can be recognized as the onset of fatigue or drowsiness when self-declared comment by a testee, comment by an observer, and video tape record are totally compared.

It should be noted that in a range stably showing a phase difference of about 180°, fatigue signal indicating fatigue and falling asleep warning signal showing indicating the onset of sleep are mixed. However, from a later-described test result, when the sleeping signal at the time of the onset of sleep (at the time of immediately after sleeping and thereafter) is taken as a criterion in the inclination of the power values, the above-described characteristic signal accompanying a phase difference of about 180° appearing just before that time becomes remarkably small in change thereafter at a large amplitude as much as twice or even greater than that of the sleeping signal, whereas in characteristic signals accompanying a phase difference of about 180° appearing at other timings, a difference in amplitude of the inclination of the power values to a signal in front and behind thereof was relatively small. In other words, since the falling asleep warning signal appears while resisting to sleep, it significantly differs from time series signals existing in front and behind thereof. However, a fatigue signal generated from peripheral fatigue, and central fatigue exists in large periodicity like a roar. Therefore, the former is determined as a falling asleep warning signal, and the latter is determined to be a fatigue signal, so that both are distinguished. It should be noted that the falling asleep warning signal is a signal showing the state of falling asleep latency which is a point of destination of the fatigue, and a kind of signal showing fatigue. Therefore, according to the present embodiment, it is possible to determine a kind whether the signal relating to fatigue in a broad sense is a fatigue signal or a falling asleep warning signal.

The comparing and determining means (comparing and determining step) 26 includes a fatigue state determining means (step). The means is to perform frequency analysis of inclination change of the power values and inclination of the maximum Lyapunov indexes appearing in time series. It is determined from the test result described later to be central fatigue predominant when the power spectrum of inclination of the maximum Lyapunov indexes is large, and to be peripheral fatigue predominant when the power spectrum of inclination of the power values is large. Through this determination, it is possible to determine the cause of the generation of the extracted fatigue signal to be due to peripheral fatigue or central fatigue.

The fatigue degree calculating means (fatigue degree calculating step) 27 has a structure to estimate an amount of energy metabolism by calculating an integral value through absolute value treatment of time series signal of power value inclination obtained from the power value inclination calculating means in the inclination calculating means 25, and to calculate the integral 20 value as the degree of fatigue (degree of progress in fatigue). The structure is based on the fact that the amount of energy metabolism links together with the degree of fatigue. With this means, it is possible to objectively grasp the degree of fatigue, and comprehensively evaluate together with a point of time to detect a fatigue signal or a falling asleep warning signal by the above-described comparing and determining means 26, so that it is possible to determine whether or not to alert, for instance, a driver. Furthermore, since the fatigue degree can be quantified, it is possible to make a driver aware himself of whether a rest is necessary or not.

The above-described embodiment includes the maximum Lyapunov index calculating means (maximum Lyapunov index calculating step), the maximum Lyapunov index peak value detecting means (maximum Lyapunov index peak value detecting step), the living body signal peak value detecting means (living body signal peak value detecting step), the power value calculating means (power value calculating step) and the inclination calculating means (inclination calculating step), and in addition, the comparing and determining means (comparing and determining step). Therefore, the above-described embodiment includes both functions of a fatigue degree measurement device and a fatigue detection device. When measuring the degree of fatigue, it is preferable to have a structure to detect timing to generate a fatigue signal except a quantitative value of the degree of fatigue, so that it is possible to effectively control the timing of generation of a warning to a driver by a warning device, or the like. However, it is also possible to form a fatigue detection device by providing a comparing and determining means to a structure without a fatigue degree calculating means.

A computer program of the present invention to be structured including the maximum Lyapunov index calculating means (maximum Lyapunov index calculating step), the maximum Lyapunov index peak value detecting means (maximum Lyapunov index peak value detecting step), the living body signal peak value detecting means (living body signal peak value detecting step), the power value calculating means (power value calculating step), the inclination calculating means (inclination calculating step), the comparing and determining means (comparing and determining step), and a fatigue degree calculating means (fatigue degree calculating step) can provide by storing into a recording medium. "A recording medium" is a medium to carry a program which cannot occupy a space by itself, which is, for instance, a flexible disk, a hard disk, a CD-ROM, a MO (magneto-optic disk), a DVD-ROM, and so on. It is also possible to transmit from a computer to install a program according to the present invention to another computer via a telecommunication line. It is possible to form a fatigue degree measurement device or a fatigue detection device according to the present invention by preinstalling or downloading the above-described program to a general-purpose terminal device.

TEST EXAMPLE (Fatigue Experiment with Short Time Seating and the Result thereof)

Short time seating experiments for 5 to 30 minutes were carried out with 13 male testees. FIGS. 7A and 7B show 30 minutes time series change of the inclinations of the power value and the maximum Lyapunov indexes of one of the testees. FIG. 7A shows data at the time when the testee is seated in a round-shouldered posture, and FIG. 7B shows data at the time when the same testee is seated on the same seat in a forced posture. Note that the round-shouldered posture is a posture to support without using muscle force and to support the posture with a ligament, while the forced posture is a posture to support the posture throwing out the testee's chest using the muscle force. Since, in general, the round-shouldered posture is the state of little muscle fatigue, central fatigue is predominant. The forced posture is peripheral fatigue predominant.

When studying the time series signal in FIGS. 7A and 7B, it is found that a change rate in inclination of the power value is gradually decreased, and inclination of the maximum Lyapunov indexes is also tending to decrease while fluctuating in the round-shoulder posture with central fatigue predominant in FIG. 7A. A fatigue signal is generated at the early stage of the experiment, and it is read that the testee became accustomed to the experiment in the latter half of the experiment, staying mentally and physically in a relaxed state. Whereas, in the forced posture with peripheral fatigue predominant in FIG. 7B, both respective inclinations of the power values and maximum Lyapunov indexes tend to increase, which is thought that the fatigue degree increases non-linearly, and physical and emotionally fatigues are generated due to strain and posture-sustaining. Accordingly, in the comparing and determining means (step) 26, when the respective inclinations of the power values and maximum Lyapunov indexes show a tendency similar to the former, the means is preferably set to determine that central fatigue is predominant, and when showing a tendency similar to the latter, it is set to determine that peripheral fatigue is predominant.

FIGS. 8A and 8B show the result of frequency analysis of the round-shoulder posture and forced posture in FIGS. 7A and 7B. From the drawings, it is found that in the state of central fatigue predominant, the power spectrum of inclination of the maximum Lyapunov index is large, while in the state of peripheral fatigue predominant, the power spectrum of inclination of the power values tends to become large. Accordingly, in the comparing and determining means (step) 26, it is preferable to have a structure to determine whether it is central fatigue predominant or peripheral fatigue predominant by comparing to find which power spectrum of inclination is larger from such a frequency analysis.

(Fatigue Experiment with Long Time Seating)

A 3-hour static seating experiment, and a 3-hour seating experiment under random excitation including passing across a protrusion, which generates impact vibration of 2.0 G in P-P value of amplitude at 1.3 Hz collected using a wagon type car in Michigan, U.S.A. were performed. Three male testees were all 20 to 30 years old and in the state of 10 to 15 minutes falling asleep latency. The time zone was from one to four pm.

For the experiment, used were a bucket type car seat (posture-sustaining type seat) regarding posture sustainability as important, having high supportability of the lumber vertebra and ischium node, and rather hard cushioning property to easily sustain a final stable posture, and a body pressure dispersing type car seat (body pressure dispersing type seat) having rather soft cushioning property, expanding a contact area, and reducing the peak value of the body pressure while taking the above-described posture sustainability as a base.

(Result of 3-Hour Static Seating Experiment)

Figure 9A:
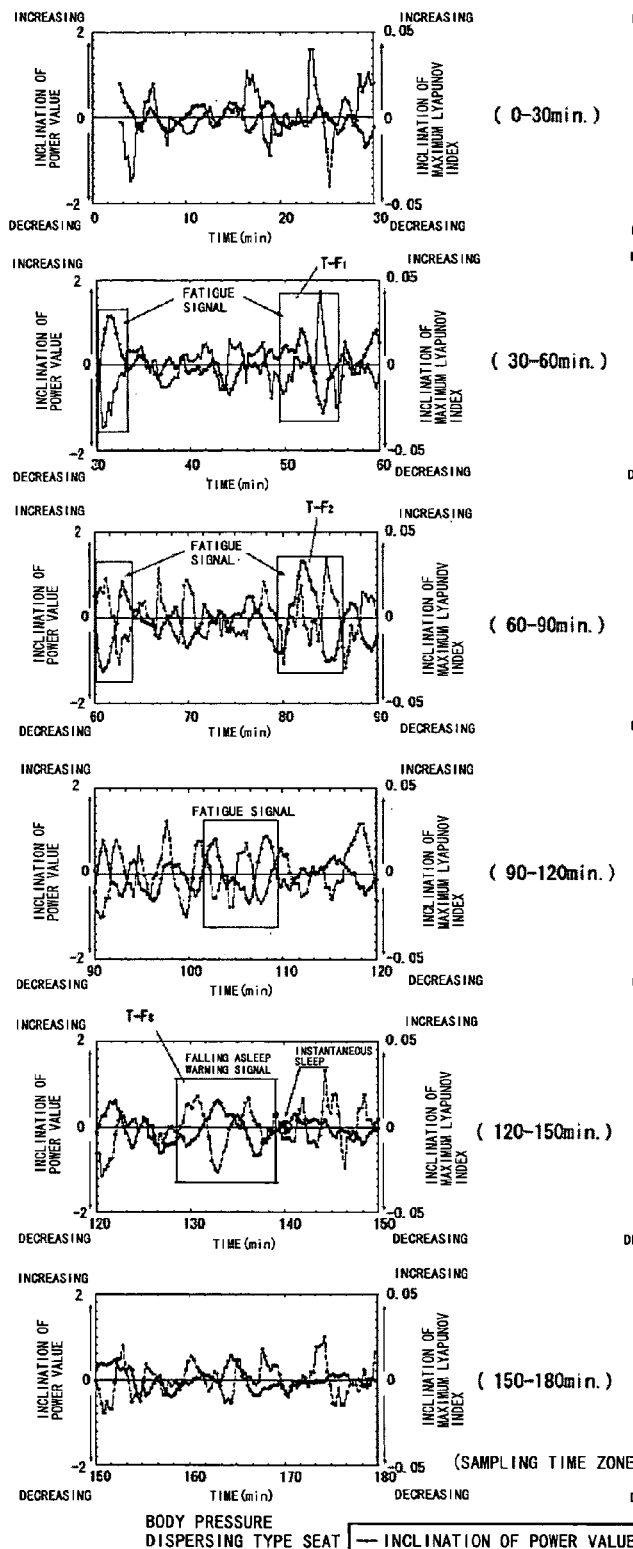
FIGS. 9A and 9B are views showing the inclinations of power value and the maximum Lyapunov index obtained from a 3-hour static seating experiment.
Figure 9B:
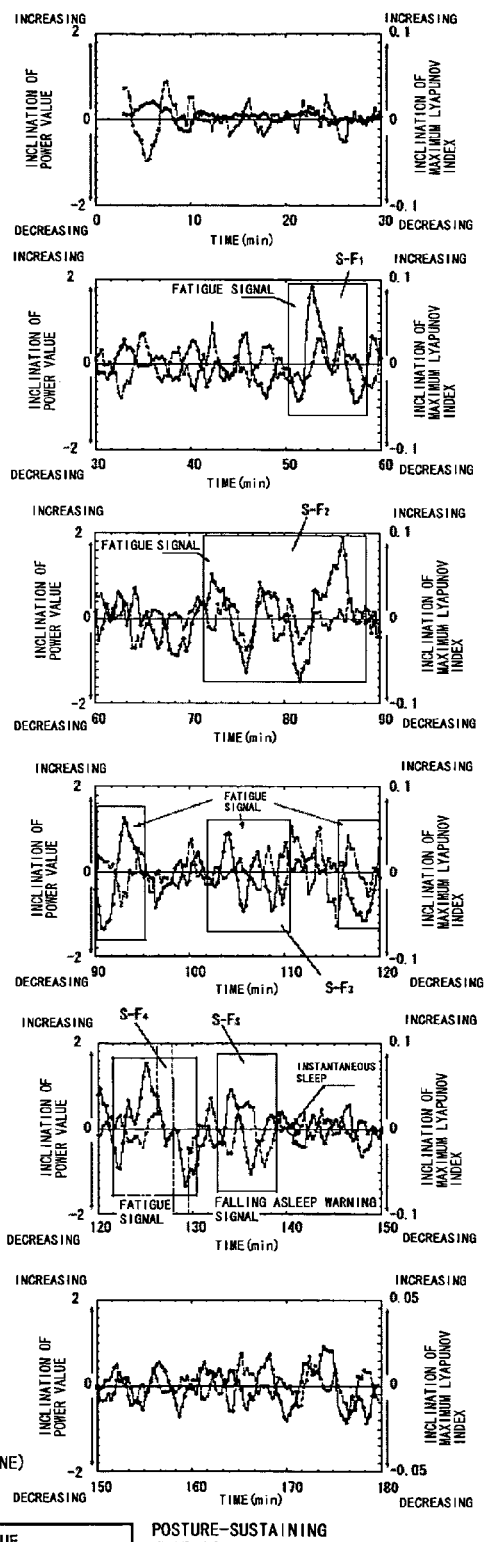

FIGS. 9A and 9B show time series changes of the inclinations of the power values and maximum Lyapunov indexes of a person among the testees for 3 hours. FIG. 9A shows for the case of seating on the body pressure dispersing type seat, and FIG. 9B shows for the case of seating on the posture-sustaining type seat.

T-F1, T-F2, T-F3, and T-Fs in FIG. 9A and S-F1, S-F2, S-F3, S-F4, and S-Fs in FIG. 9B show signal groups in which the above-described characteristic signals appeared. Among them, since the absolute values of T-Fs and S-Fs are small compared with other signals, and change of the inclination of the power values after that becomes small, they are identified as the falling asleep warning signals. It can be determined that instantaneous sleep occurs 140 minutes after the falling asleep warning signal. This is considered that the falling asleep warning signal is in a dangerous region in terms of a fatigue curve, and since the amplitude of the signal becomes small, though its wave height coefficient rapidly increases, its absolute value becomes small. In contrast, in T-F1, T-F2, T-F3, S-F1, S-F2, S-F3, and S-F4, the amplitude tends to increase and their absolute values are great. Accordingly, since these signals have characteristics different from the falling asleep warning signals, they are determined to be fatigue signals. Whereas, as seen in the body pressure dispersing type seat, when the amplitude of the fatigue signal decreases, rhythm is stabilized, and it approaches to a steady state, it can be determined that the central fatigue is predominant, by referring to the result in FIGS. 7A and 7B.

FIG. 10A is a view showing frequency analysis of the inclination of the power values, and frequency analysis of the inclination of the maximum Lyapunov indexes of the body pressure dispersing type seat in FIG. 9A, while FIG. 10B is a view showing frequency analysis of the inclination of the power values, and frequency analysis of the inclination of the maximum Lyapunov indexes of the posture-sustaining type seat in FIG. 9B.

FIG. 11A shows respective fatigue degrees of the body pressure dispersing type seat in FIG. 9A and the posture-sustaining type seat in FIG. 9B by absolute value treatment of time series signals of the power value inclination and calculation as integral values. FIG. 11A also shows graphing of respective sensory evaluation values together with the fatigue degrees (calculated values). Note that the sensory evaluation values are shown based on Borg index (refer to "Seat Sensory Quality Evaluation", The Society Automotive Engineers of Japan, Academic Lecture Meeting, Preprint Collection, No. 91-99, 21-24, 2002). Whereas, FIG. 11B shows qualitative evaluation of the posture-sustaining type seat on the basis of the body pressure dispersing type seat.

It is recognized from FIGS. 11A and 11B that the fatigue curve shown by the fatigue degree (calculated value) determined with the fatigue degree measurement device according to the present invention) and the fatigue curve based on the sensory evaluation value are quite similar to each other in qualitative trend, so that the fatigue degree can be shown quantitatively and objectively by the fatigue degree measurement device according to the present invention.

When considering the frequency analysis in FIGS. 10A and 10B and the fatigue curves in FIGS. 11A and 11B, it is recognized that the body pressure dispersing type seat has high posture sustainability and can easily follow posture change so that a testee can continue seating in a relaxed state. Furthermore, the frequency analysis of the inclination of the maximum Lyapunov indexes shows the fatigue signal in increasing trend and instantaneous sleep due to central fatigue starts about 140 minutes after start of the experiment (see FIG. 9A), but since respective steps of the frequency analysis of the inclination of the power values and the fatigue curves move nearly linearly, it is found that the body pressure dispersing type seat affords less feeling of fatigue.

On the other hand, in the posture-sustaining type seat, the muscle of the testee supports the posture, and a very favorable feeling of seating is shown until 30 minutes, but a feeling of fatigue rapidly develops from after 30 minutes when muscle fatigue starts, and the fatigue signals are generated intermittently. In other words, the testee starts instantaneous sleeping 140 minutes after the start of the experiment even on this seat, but since the amplitude of the fatigue signals are in increasing trend, it is assumed from the fatigue curve for 120 to 150 minutes that it is instantaneous sleep due to physical fatigue and reduction of the fatigue degree is after instantaneous sleep and body motion (refer to FIG. 9B, and FIGS. 11A and 11B). It is also understood from the frequency analysis of the inclination of the power value in FIG. 10 that more energy is consumed compared with the body pressure dispersing type seat. From the frequency analysis of the inclination of the maximum Lyapunov indexes, since fluctuation of the fatigue signals has an increasing tendency, it is considered that the testee is strained and in high mental excitement.

Thus, the present invention can be used for objective evaluation of a seat from its fatigue curve obtained by calculating the fatigue degree, and frequency analysis of the inclinations of the power value and maximum Lyapunov indexes.

(Result of 3-Hour Seating Experiment Under Random Excitement)

Figure 12A:
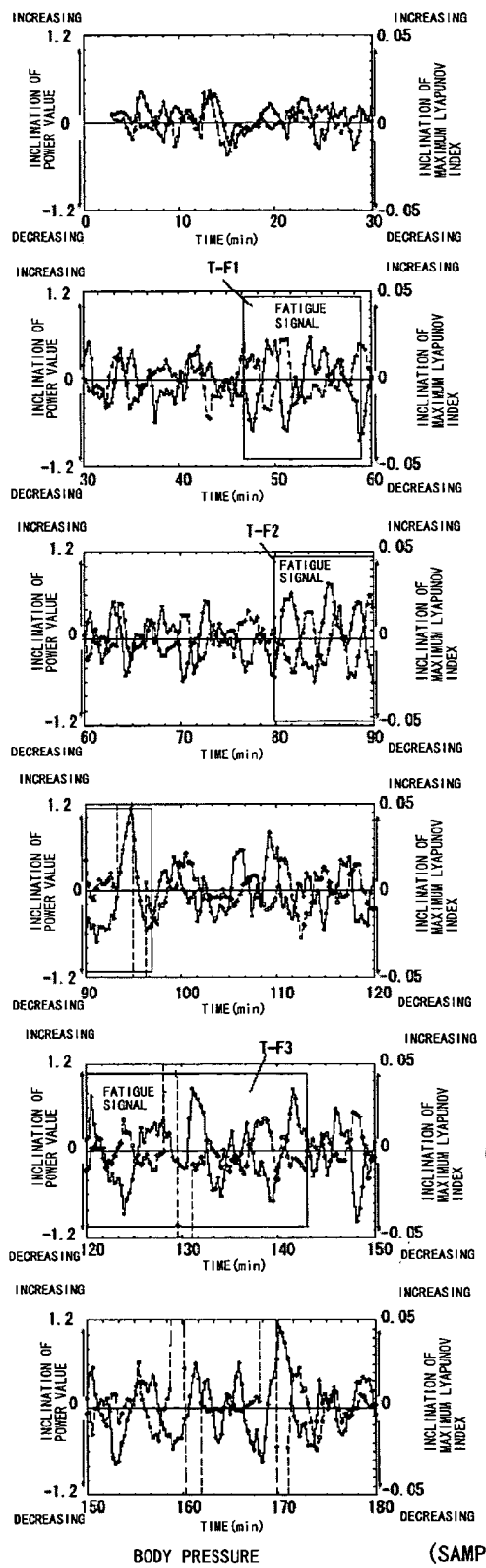
FIG. 12A and 12B are views showing the inclinations of power value and the maximum Lyapunov index obtained by 3-hour seating experiment under random excitation.
Figure 12B:
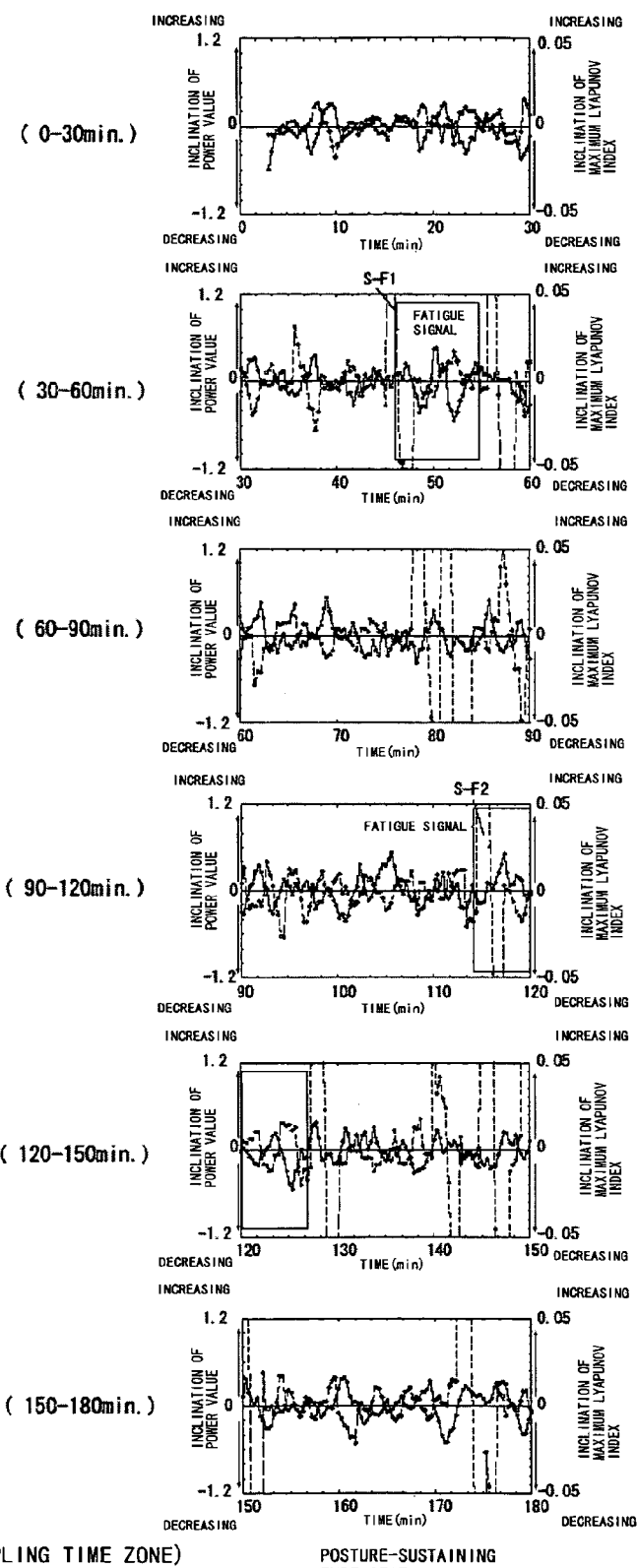

FIGS. 12A, 12B, and 12C are views showing 3-hour time series change of the inclinations of the power value and maximum Lyapunov indexes of one testee among the testees. FIG. 12A shows a case of seating on a body pressure dispersing type seat, and FIG. 12B shows a case of seating on a posture-sustaining type seat.

FIG. 13A is a view showing frequency analysis of the inclinations of the power values and maximum Lyapunov indexes of the body pressure dispersing type seat in FIG. 12A, while FIG. 13B is a view showing frequency analysis of the inclinations of the power values and maximum Lyapunov indexes of the posture-sustaining type seat in FIG. 12B.

FIG. 14A shows respective fatigue degrees of the body pressure dispersing type seat in FIG. 12A and the posture-sustaining type seat in FIG. 12B by absolute value treatment of time series signals of the power value inclination and calculation as integral values. FIG. 14A also shows graphs of respective sensory evaluation values together with the fatigue degrees (calculated values). FIG. 14B is the fatigue curve evaluating the fatigue degrees (calculated values) and the sensory evaluation values of the body pressure dispersing type seat on the basis of the posture-sustaining type seat.

In the fatigue curves in FIG. 14A, the degree of fatigue shown by the calculated value and the sensory evaluation value is nearly consistent for the body pressure dispersing type seat till 150 minutes and for the posture-sustaining type seat till 120 minutes. The difference from the sensory evaluation value after 120 minutes is due to the effect of lumbago caused by the beating by the seat back against the waist portion caused by vertical vibration, and the difference from the sensory evaluation values after 150 minutes is considered due to numbness. When seeing FIG. 14B on this point, a qualitative trend of the calculated values and the sensory evaluation values are well consistent with each other till 150 minutes, but it shows a tendency of dissociation after 150 minutes. FIGS. 12A and 12B shows that in the case of the posture-sustaining type seat, changes of the inclinations of the power values and maximum Lyapunov indexes are extremely restrained. This is considered to be because that a testee on the posture-sustaining type seat is kept seated bearing a pain. Note that signal in which the inclination of the maximum Lyapunov indexes is shaken completely among the time series signals shows occurring of body movement.

It is said from FIGS. 13A and 13B that the body pressure dispersing type seat shows linearly fatigue changes within the time of experiment, the testee can seat in a suitable fluctuation and a large fatigue promotion cannot be found. Whereas in the posture-sustaining type seat, testees use the muscle force in the early stage of experiment, and try to recover using other muscles by body movement. However, the muscle to sustain the posture is in the direction of convergence, and a feeling of fatigue is seen to be rapidly increased.

(Seating (Sitting Posture) Vehicle Driving Experiment)

The experiment is carried out on a driver's seat and a passenger seat using a sedan type vehicle. A testee on the driver's seat is a 40-years male in falling instantaneous sleep latency for 10 to 15 minutes, and a testee on the passenger seat is a 30-years female in falling asleep latency for 10 to 15 minutes. The finger-tip volume pulse wave collected for 3.5 hours from one thirty to five o'clock in the afternoon between Katsuragawa Parking Area (PA) in Meishin Highway to Kibi Service Area (SA) in Sanyo Highway, and Kibi SA to Kodani SA. Both of the testee on the driver's seat and the testee on the passenger seat executed two-hour driving before starting the experimental driving.

(Result of Seating (Sitting Posture) Vehicle Driving Experiment)

Figure 15A:
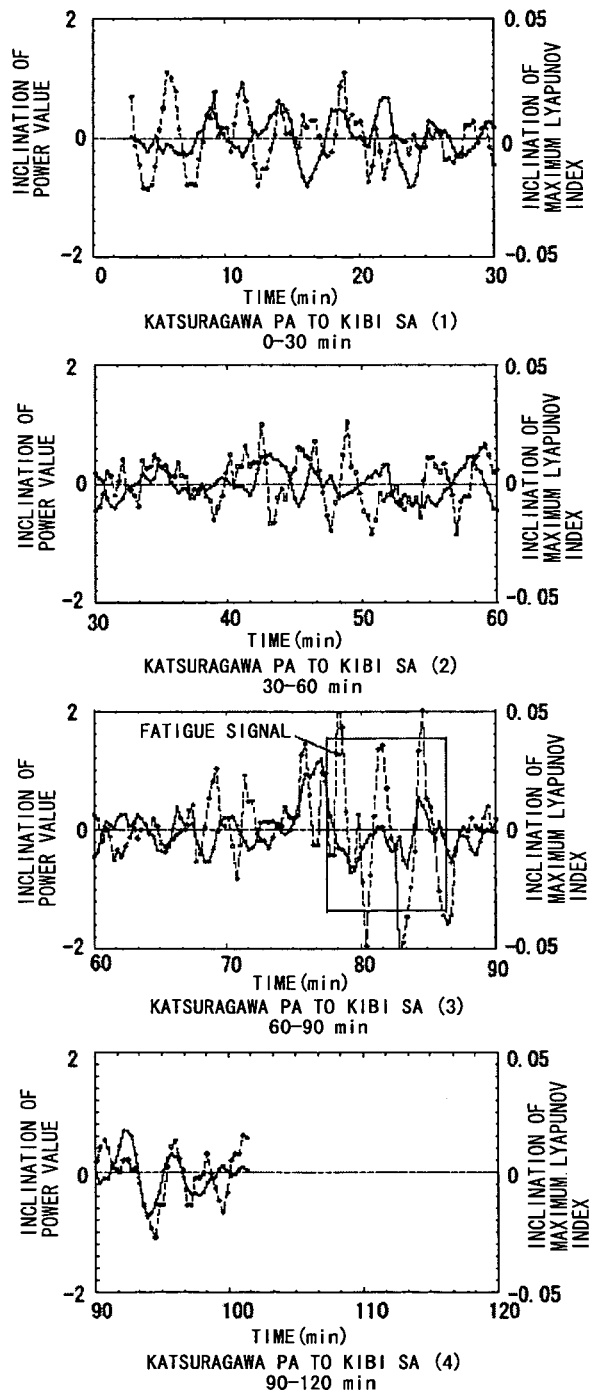
FIGS. 15A and 15B are views showing the inclinations of power value and the maximum Lyapunov index of a testee on a driver's seat obtained during a seated (seated posture) vehicle driving experiment.
Figure 15B:
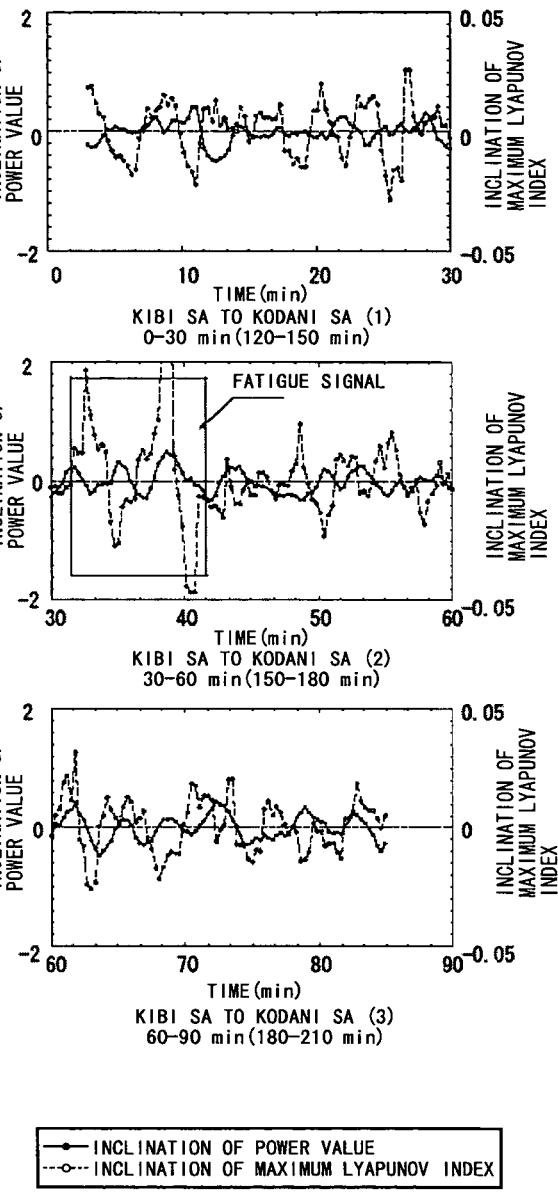

FIGS. 15A and 15B show time series signals of the inclinations of the power value and maximum Lyapunov indexes of the testee on the driver's seat, and FIGS. 16A and 16B show frequency analysis of the inclinations of the power values and maximum Lyapunov indexes in FIGS. 15A and 15B. From this result, it is found that in the testee on the driver's seat, awakening and fatigue are periodically generated for 100 minutes when driving from Katsuragawa PA to Kibi SA, and the state of awakening in a medium degree is kept. Then, physical fatigue is generated from 75 minutes to 90 minutes, and adaptability is enhanced due to strain. This point can be presumed from the fact that the power spectrum of the inclination of the maximum Lyapunov indexes found in the result of the frequency analysis in FIGS. 16A and 16B becomes large.

The second fatigue is generated 40 minutes after resumption of the driving during driving between Kibi SA and Kodani SA. In this fatigue, as shown in the result of the frequency analysis, no increase in the power spectrum of the inclination of the power values is seen, and as understood from the fatigue curve shown by the arrow a in FIG. 19A, the fatigue degree is lower than the time of driving between Katsuragawa PA to Kodani SA. That is, from these results, the central fatigue is presumed to be predominant, and it is adapted to the central fatigue by strain. Note that this central fatigue is restored after 10 minutes.

Both observation and self-declaration are in agreement on this point.

From the frequency analysis in FIGS. 16A and 16B, inclination of the power values is in increasing trend between Katsuragawa PA and Kibi SA, and it is found that driving is carried out using physical strength with relatively relaxing. On the other hand, fatigue is generated at mid point between Kibi SA and Kodani SA, but strain is enhanced to cope with a feeling of fatigue. In other words, the testee on the driver's seat is supposed to drive using physical strength, and when fatigue is developed, the testee generates rhythm with mental strength to cope with the fatigue.

Figure 17:
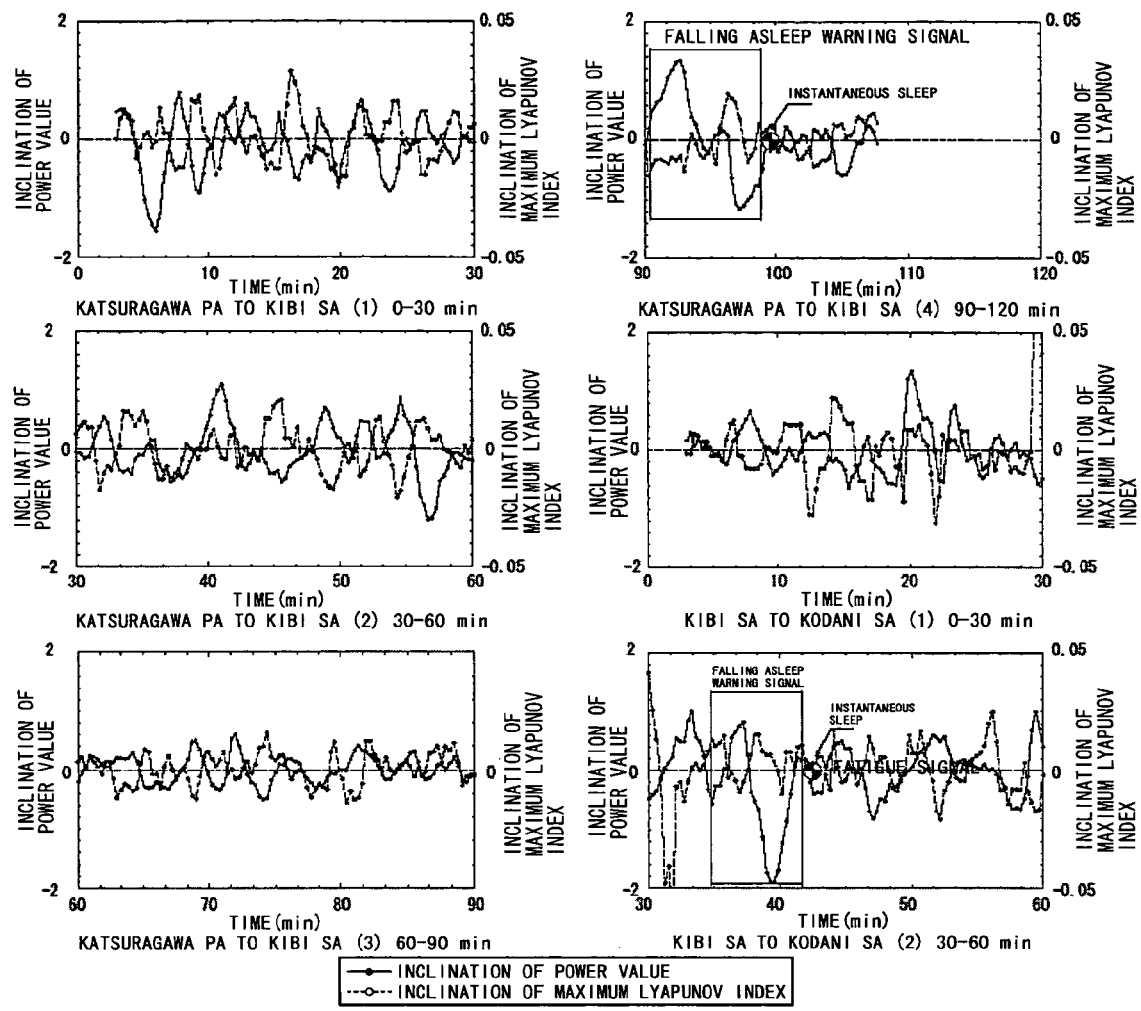
FIGS. 17A and 17B are views showing the inclinations of power value and the maximum Lyapunov index of a testee on a passenger seat obtained during a seated (seated posture) vehicle driving experiment.
Figure 18:
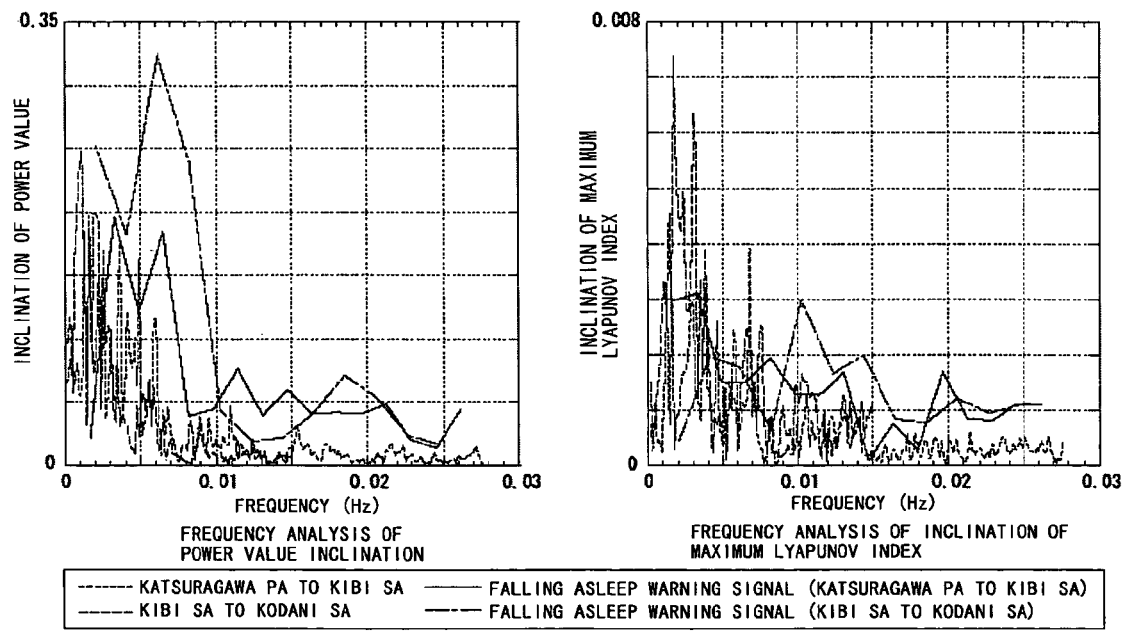
FIGS. 18A and 18B are views showing a result of frequency analysis in FIGS. 17A and 17B.

FIG. 17 shows time series signals of the inclinations of the power values and maximum Lyapunov indexes of the testee seated on the passenger seat. The testee was in a fatigue state due to driving for two hours before collecting the living body signal. This is presumed from rapid rise of the fatigue curve shown 5 minutes after leaving Katsuragawa PA as shown by an arrow b in the fatigue curve in FIG. 19B. A falling asleep warning signal and instantaneous sleep are generated between 90 minutes to 100 minutes. It is supposed to be developed by accumulated physical fatigue together with central fatigue, because the result of the frequency analysis in FIGS. 18A and 18B show both of high level power spectrums of the respective inclinations of the power values and maximum Lyapunov indexes. Instantaneous sleep appeared about 5 minutes after generating a falling asleep warning signal, the testee temporarily restored and took a rest at Kibi SA. After driving again, a second falling asleep signal is developed 40 minutes thereafter. Then, instantaneous sleep is developed 5 minutes thereafter, and the driving state is shifted to the state of awakening. It is understood that the testee is in a fatigue state in general from the rate of increase and decrease in amplitude of the power values of the time series signals to the time to keep the opposite state. Incidentally, adaptability of the testee is increased after the instantaneous sleep between Kibi SA and Kodani SA, mental strength is enhanced due to expectation of homing, which results in restoring from a feeling of fatigue. This point can be recognized from the frequency analysis in FIGS. 18A and 18B. Moreover, observation was in agreement with comment by the testee.

Figure 19A:
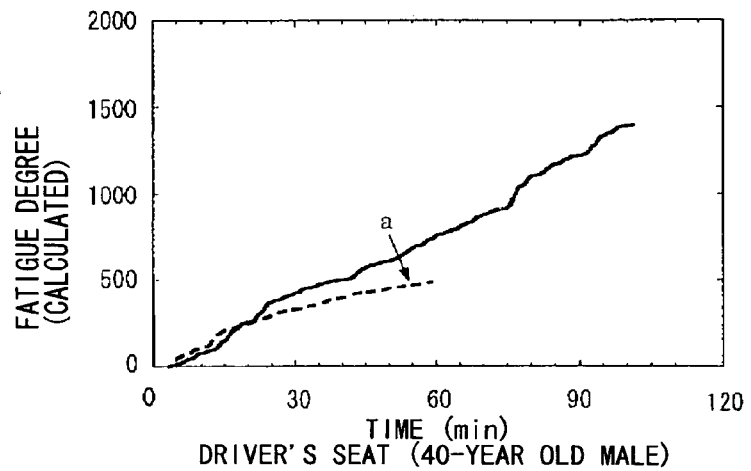
FIGS. 19A, 19B, and 19C are views showing calculated values on fatigue degrees.
Figure 19B:
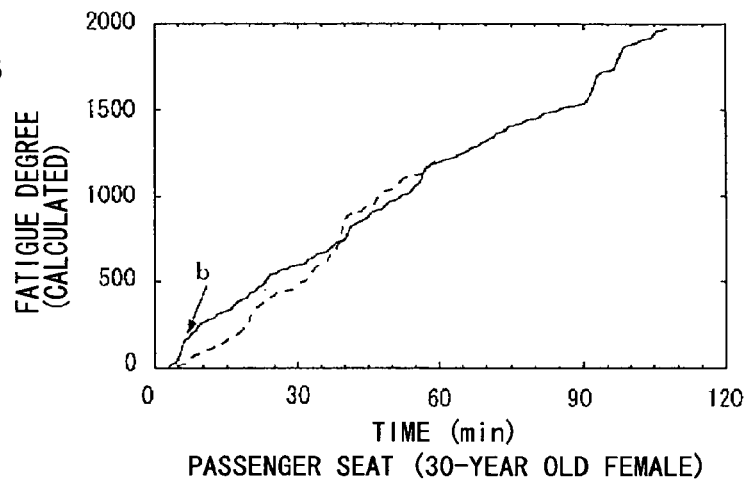
Figure 19C:
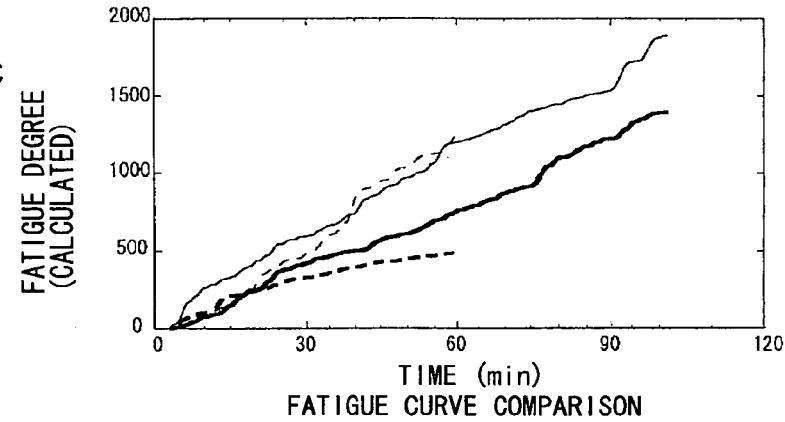

Whereas, FIGS. 19A, 19B, and 19C show calculated fatigue degrees. FIG. 19A is the fatigue curve of a testee on the driver's seat. FIG. 19B is the fatigue curve of a testee on the passenger seat and FIG. 19C is a view in which both fatigue curves are overlapped. From this fatigue curves, it is understood that the transition tendency to fatigue degree due to difference in physical strength between male and female, in driving or not in driving, or a difference in mental conditions such as expectation of homing or the like is well grasped. FIG. 20 shows comparison of wave height coefficients among falling asleep signals, fatigue signals, and sleep signals by the vehicle driving experiment. The wave height coefficient is in a relatively high level because the experiment is in an environment to receive external stimuli.

Moreover, change of the fatigue degree expressed by calculation in FIGS. 19A, 19B, and 19C are in good agreement with the feeling and comment of the testees, which proves that calculation of the fatigue degree according to the present invention is effective in the case of driving actual cars.

(Lumbago Acceleration Short Time Seating Experiment)

The experiment is carried out by three male testees with different physiques using a seat in which tip urethane of 30 mm in thickness is put on the seat cushion, and a detachable and thickness-adjustable urethane is placed on a lumber vertebra supporting portion on the seat back. Characteristics of the three testees are a muscular type testee, a lumbago carrying testee, and a leptsome testee. The experiment is performed while changing the following three kinds of postures: the free posture without a back rest, the posture similar to the spinal curve when standing (natural driving posture) and the posture stressing waist overhang.

(Result of the Lumbago Acceleration Short Time Seating Experiment)

FIGS. 21A, 21B, and 21C show frequency analysis and fatigue curves of the inclinations of the power values and maximum Lyapunov indexes in the present experiment. FIG. 21A shows data for the muscular type testee, FIG. 21B shows data for the lumbago carrying testee, and FIG. 21C shows data for the leptsome testee. From these drawings, it is understood that in the case of the lumbargo carrying testee, not like the two other testees, the fatigue degree rises at an early stage, and in the case of no backrest, the testee bears an ache. The muscular testee and leptsome testee show a relatively stable state irrespective of difference in the method of supporting posture by the seat. Especially, it can be seen that the muscular testee can sustain his posture with back muscles and abdominal muscles. Incidentally, the fatigue degree differs in progress of the fatigue by their physical strengths. These points were in good agreement with comment by the testees.

Accordingly, in this experiment, it is understood that the detection of fatigue and the measurement of fatigue degree according to the present invention can show the fatigue and the fatigue degree objectively and quantitatively.

INDUSTRIAL APPLICABILITY

As described above, the present invention is possible to quantify the degree of fatigue and objectively calculate not only central fatigue but also physical fatigue. It is also possible to determine the timing of creation of a fatigue signal and falling asleep warning signal, and their kinds from the state of time series signals of the inclinations of the power values and maximum Lyapunov indexes shown in the process of calculating the fatigue degree, and conditions of a frequency analysis. Accordingly, it is possible to make an arbitrary warning device function in the case of approaching the prescribed fatigue degree or in the case of detecting a fatigue signal or falling asleep warning signal, using these means. Furthermore, since the degree of fatigue can be displayed objectively and a fatigue signal and a falling asleep warning signal can be detected, it is possible to use the present invention for performance evaluation of a human seating seat or a bed. At the same time, it is also possible to use the present invention for a diagnostic device to grasp the user's state of mind and body in such a case. It is also conceivable to apply the present invention to execute, for instance, trouble checking of machinery by using a measurement device to detect minute vibration of a machine instead of the living body signal data.

The invention claimed is:

1. A fatigue degree measurement device, comprising:
   a living body signal peak value detecting means for detecting the peak value in each cycle of an original waveform of the living body signal data collected by a living body signal measurement device;
   a power value calculating means for calculating the difference between a peak value on the upper limit side and a peak value on the lower limit side for every prescribed time period from each peak value obtained by said living body signal peak value detecting means and for setting the difference as the power value;
   a power value inclination calculating means for determining an inclination of said power values to the time base during the prescribed time period by slide calculating the prescribed times at a prescribed overlap rate for the prescribed time period;
   a fatigue degree calculating means for calculating an integral value by absolute value treatment of time base signal of power value inclination obtained from the slide calculation by said power value inclination calculating means to determine the obtained integral value as the degree of fatigue;
   a maximum Lyapunov index calculating means for calculating the maximum Lyapunov index by chaos analyzing said living body signal data;
   a maximum Lyapunov index peak value detecting means for detecting the peak value in each cycle of a time series change waveform of the calculated maximum Lyapunov index;
   a maximum Lyapunov index inclination calculating means for determining an inclination of each peak value of the maximum Lyapunov indexes obtained by the maximum Lyapunov index peak value detecting means to the time base during the prescribed time period by slide calculating the prescribed times at a prescribed overlap rate for the prescribed time period, in addition to said inclination of the power value; and
   a comparing and determining means for determining as the generating point of a fatigue signal when the inclination of the power value obtained by slide calculating using said power value inclination calculating means and the maximum Lyapunov index obtained by slide calculating using the maximum Lyapunov index inclination calculating means stably showing the phase difference of substantially 180° among time series signals,
   wherein said comparing and determining means includes a fatigue state determining means for determining the state of fatigue based on the inclinations of power value and the maximum Lyapunov index appearing in time series, and
   wherein said fatigue state determining means includes a means to perform frequency analysis of the change in the inclinations of power value and the maximum Lyapunov index appeared in time series, and determines a central fatigue predominant state when the power spectrum of the inclination of the maximum Lyapunov index is large, and a peripheral fatigue predominant state when the power spectrum of the inclination of the power value is large.

2. The fatigue degree measurement device according to claim 1,
   wherein said living body signal peak value detecting means is a means to perform smoothing differentiation of the living body signal data to determine the peak value on the upper limit side and the peak value on the lower limit side for the width fluctuation of the waveform with a predetermined threshold value.

3. The fatigue degree measurement device according to claim 1,
   wherein said power value calculating means is a means to calculate the difference between the mean value of the peak value on the upper limit side and the mean value of the peak value on the lower limit side within the prescribed time period range of the living body signal data as the power value.

4. The fatigue degree measurement device according to claim 3,
   wherein said power value calculating means is a mean to calculate the square value of the difference between the mean value of the peak value on the upper limit side and the mean value of the peak value on the lower limit side within the prescribed time period range of the living body signal data as the power value.

5. The fatigue degree measurement device according to claim 1,
   wherein the time interval used in the slide calculation in said power value inclination calculating means is 180 seconds and the overlap rate is 90%.

6. The fatigue degree measurement device according to claim 1,
   wherein said maximum Lyapunov index peak value detecting means is a means to perform smoothing differentiation of the time series change waveform of the maximum Lyapunov index to determine the peak value on the upper limit side and the peak value on the lower limit side for the width fluctuation of the waveform with a predetermined threshold value.

7. The fatigue degree measurement device according to claim 1, wherein the time interval used in the slide calculation in said maximum Lyapunov index inclination calculating means is 180 seconds and the overlap rate is 90%.

8. A fatigue detection device, comprising:

a living body signal peak value detecting means for detecting the peak value in each cycle of an original waveform of the living body signal data collected by a living body signal measurement device;

a power value calculating means for calculating the difference between a peak value on the upper limit side and a peak value on the lower limit side for every prescribed time period from each peak value obtained by said living body signal peak value detecting means and for setting the difference as the power value;

a power value inclination calculating means for determining an inclination of said power values to the time base during the prescribed time period by slide calculating the prescribed times at a prescribed overlap rate for the prescribed time period;

a maximum Lyapunov index calculating means for calculating the maximum Lyapunov index by chaos analyzing said living body signal data;

a maximum Lyapunov index peak value detecting means for detecting the peak value in each cycle of a time series change waveform of the calculated maximum Lyapunov index;

a maximum Lyapunov index inclination calculating means for determining an inclination of each peak value of the maximum Lyapunov indexes obtained by said maximum Lyapunov index peak value detecting means to the time base during the prescribed time period by slide calculating the prescribed times at a prescribed overlap rate for the prescribed time period; and a comparing and determining means for determining as the generating point of a fatigue signal when the inclination of the power value obtained by slide calculating using said power value inclination calculating means and the maximum Lyapunov index obtained by slide calculating using said maximum Lyapunov index inclination calculating means stably showing the phase difference of substantially 180° among time series signals, wherein said comparing and determining means includes a fatigue state determining means for determining the state of fatigue based on the inclinations of power value and the maximum Lyapunov index appearing in time series, and wherein said fatigue state determining means includes a means to perform frequency analysis of the change in the inclinations of power value and the maximum Lyapunov index appeared in time series, and determines a central fatigue predominant state when the power spectrum of the inclination of the maximum Lyapunov index is large, and a peripheral fatigue predominant state when the power spectrum of the inclination of the power value is large.

9. The fatigue detection device according to claim 8, wherein said living body signal peak value detecting means is a means to perform smoothing differentiation of the living body signal data to determine the peak value on the upper limit side and the peak value on the lower limit side for the width fluctuation of the waveform with a predetermined threshold value, and said maximum Lyapunov index peak value detecting means is a means to perform smoothing differentiation of the time series change waveform of the maximum Lyapunov index to determine the peak value on the upper limit side and the peak value on the lower limit side-for the width fluctuation of the waveform with a predetermined threshold value.

10. The fatigue detecting measurement device according to claim 8, wherein the time interval used in the slide calculation in said power value inclination calculating means and said maximum Lyapunov index inclination calculating means is 180 seconds and the overlap rate is 90%.

11. A program, embodied on a computer readable medium, to make a computer execute a process to measure the degree of fatigue by analyzing the living body signal data collected by a living body signal measurement device to measure a human living body signal, comprising:

a living body signal peak value detecting step of detecting the peak value in each cycle of the original waveform of said living body signal data;

a power value calculating step of calculating the difference between a peak value on the upper limit side and a peak value on the lower limit side for every prescribed time period from each peak value obtained from said living body signal peak value detecting step to set the difference as the power value;

a power value inclination calculating step of determining the inclination of said power value to the time base during the prescribed time period by slide calculating the prescribed times at a prescribed overlap rate for the prescribed time period; and a fatigue degree calculating step of calculating an integral value by absolute value treatment of the time base signal of the power value inclination obtained from slide calculation by said power value inclination calculating step to determine the obtained integral value as the degree of fatigue;

a maximum Lyapunov index calculating step of calculating the maximum Lyapunov index by chaos analyzing said living body signal data;

a maximum Lyapunov index peak value detecting step of detecting the peak value in each cycle of a time series change waveform of the calculated maximum Lyapunov index;

a maximum Lyapunov index inclination calculating step of determining the inclination of each peak value of the maximum Lyapunov indexes obtained by said maximum Lyapunov index peak value detecting step to the time base during the prescribed time period by slide calculating the prescribed times at a prescribed overlap rate for the prescribed time period; and comparing and determining step of determining as the generating point of a fatigue signal when inclination of the power value obtained by slide calculating using said power value inclination calculating step and the maximum Lyapunov index obtained by slide calculating using said maximum Lyapunov index inclination calculating step stably showing the phase difference of substantially 180° among time series signals, wherein said comparing and determining step includes a fatigue state determining step to perform frequency analysis of the change in inclination of the power value and of the maximum Lyapunov index appearing in time series, and determines to be a central fatigue predominant state when the power spectrum of the inclination of the maximum Lyapunov index is large, and to be a peripheral fatigue predominant state when the power spectrum of the inclination of the power value is large.

12. A program, embodied on a computer readable medium, to make the computer execute a process to detect fatigue by analyzing the living body signal data collected by a living body signal measurement device to measure a human living body signal, comprising:

a living body signal peak value detecting step of detecting the peak value in each cycle of the original waveform of the living body signal data collected by a living body signal measurement device;

a power value calculating step of calculating the difference between a peak value on the upper limit side and a peak value on the lower limit side for every prescribed time period from each peak value obtained from said living body signal peak value detecting means to set the difference as the power value;

a power value inclination calculating step of determining the inclination of the power value to the time base during the prescribed time period by slide calculating the prescribed times at a prescribed overlap rate for the prescribed time period;

a maximum Lyapunov index calculating step of calculating the maximum Lyapunov index by chaos analyzing said living body signal data;

a maximum Lyapunov index peak value detecting step of detecting the peak value in each cycle of a time series change waveform of the calculated maximum Lyapunov index;

a maximum Lyapunov index inclination calculating step of determining the inclination of each peak value of the maximum Lyapunov indexes obtained by said maximum Lyapunov index peak value detecting step to the time base during the prescribed time period by slide calculating the prescribed times at a prescribed overlap rate for the prescribed time period, and comparing and determining step of determining as the generating point of a fatigue signal when inclination of the power value obtained by slide calculating using said power value inclination calculating step and the maximum Lyapunov index obtained by slide calculating using said maximum Lyapunov index inclination calculating step stably showing the phase difference of substantially 180° among time series signals, wherein said comparing and determining step includes a fatigue state determining step to perform frequency analysis of the change in inclination of the power value and of the maximum Lyapunov index appearing in time series, and determines to be a central fatigue predominant state when the power spectrum of the inclination of the maximum Lyapunov index is large, and to be a peripheral fatigue predominant state when the power spectrum of the inclination of the power value is large.

* * * * *